United States Patent [19]
Armistead et al.

[11] Patent Number: 5,935,954
[45] Date of Patent: Aug. 10, 1999

[54] COMPOUNDS WITH IMPROVED MULTI-DRUG RESISTANCE ACTIVITY

[75] Inventors: David M. Armistead, Maynard; Jeffrey O. Saunders, Acton, both of Mass.

[73] Assignee: Vertex Pharmaceuticals Incorporated, Cambridge, Mass.

[21] Appl. No.: 08/961,551

[22] Filed: Oct. 30, 1997

Related U.S. Application Data

[62] Division of application No. 08/626,259, Mar. 29, 1996, Pat. No. 5,717,092.

[51] Int. Cl.[6] ...................... C07D 211/60; C07D 401/12; C07D 409/12; A61K 31/445
[52] U.S. Cl. .................................... 514/235.2; 514/235.5; 514/237.2; 514/343; 514/422; 514/423; 544/124; 544/141; 544/143; 544/59; 544/186; 544/187; 544/193; 544/194; 544/360; 544/372; 546/279.1; 548/517; 548/518; 548/531; 548/536
[58] Field of Search .................................... 548/517, 518, 548/531, 536; 546/279.1; 544/124, 141, 143; 514/235.2, 235.5, 237.2, 343, 422, 423

[56] References Cited

U.S. PATENT DOCUMENTS

| | | | |
|---|---|---|---|
| 4,920,218 | 4/1990 | Askin | 540/456 |
| 5,192,773 | 3/1993 | Armistead | 514/211 |
| 5,330,993 | 7/1994 | Armistead | 514/330 |
| 5,620,971 | 4/1997 | Armistead et al. | 514/212 |

FOREIGN PATENT DOCUMENTS

| | | | |
|---|---|---|---|
| A-0457163 | 11/1991 | European Pat. Off. | C07C 233/47 |
| A-2247456 | 3/1992 | European Pat. Off. | C07D 405/14 |
| A-0515071 | 11/1992 | European Pat. Off. | C07D 498/18 |
| WO 92/00278 | 1/1992 | WIPO | C07D 211/60 |
| WO 92/19593 | 11/1992 | WIPO | C07D 207/16 |
| WO 93/00427 | 1/1993 | WIPO . | |
| WO 94/07858 | 4/1994 | WIPO | C07D 211/60 |
| WO 96/06097 | 2/1996 | WIPO | C07D 471/04 |
| WO 96/40633 | 12/1996 | WIPO | C07D 207/16 |

OTHER PUBLICATIONS

G. Blaschke et. al., "Investigation of Chromatographic Resolutions of Racemates, VI. Polymeric Amino Acid Derivatives As Optically Active Adsorbents," *Chem. Ber.*, 109(6), pp. 1967–1975 (1976).

D. Boesch et. al., "In Vivo Circumvention of P–Glycoprotein–Mediated Multidrug Resistance of Tumor Cells with SDZ PSC 833," *Cancer Res.*, 51, pp. 4226–4233 (1991).

A.M. Cameron, et al., "Immunophilin FK506 Binding Protein Associated With Inositol 1,4,5–Trisphosphate Receptor Modulates Calcium Flux," *Proc. Natl. Acad. Sci. USA*, 92, pp. 1784–1788 (Feb., 1995).

A.M. Cameron, et al., "Calcineurin Associated with the Inositol 1,4,5–Trisphosphate Receptor–FKBP12 Complex Modulates $Ca^{2+}$ Flux," *Cell* 83, pp. 463–472 (Nov., 1995).

R. S. Coleman, et. al., "Degradation and Manipulations of the Immunosuppressant FK506: Preparation of Potential Synthetic Intermediates," *Heterocycles*, 28, pp. 157–161 (1989).

M. Egbertson and S.J. Danishefsky, "Synthetic Route to the 'Tricarbonyl' Region of FK–506," *J. Org. Chem.* 54, pp. 11–12 (1989).

B.G. Gold, et al., "FK506, an Immunosuppressant, Increases Functional Recovery and Axonal Regeneration in the Rat Following Axotomy of the Sciatic Nerve," *Soc. Neurosci. Abs.*, 19, p. 1316 (1993).

B.G. Gold, et al., "The Immunosuppressant FK506 Increases the Rate of Axonal Regeneration in Rat Sciatic Nerve," *Journal of Neuroscience*, 15, pp. 7509–7516 (Nov., 1995).

M.T. Goulet and J. Boger, "Degradative Studies on the Tricarbonyl Containing Macrolide Rapamycin", *Tetrahedron Lett.*, 31, pp. 4845–4848 (1990).

W.N. Hait, et al., "Activity of Cyclosporin A and a Non-–Immunosuppressive Cyclosporin Against Multidrug Resistant Leukemic Cell Lines", *Cancer Commun.*, 1(1), pp. 35–43 (1989).

M.W. Harding, et al., "A Receptor for the Immunosuppressant FK–506 is a Cis–Trans Peptidyl–Prolyl Isomerase", *Nature*, 341, pp. 758–760 (1989).

J.R. Hauske, et al., "Design and Synthesis of Novel FKBP inhibitors," *J. Med. Chem.*, 35, pp. 4284–4296 (1992).

J.R. Hauske, et al., "Investigation of the Effects of Synthetic, Non–Cytotoxic Immunophilin Inhibitors of MDR", *Bioorg. & Med. Chem. Lett.*, 4, pp. 2097–2102 (1994).

Holt, D. et al., "Design, Synthesis, and Kinetic Evaluation of High–Affinity FKBP Ligands and the X–ray Crystal Structures of Their Complexes with FKBP12," *J. Am. Chem.*, 115, 9925–9938 (1993).

W.E. Lyons, et al., "Immunosupressant FK506 Promotes Neurite Outgrowth in Cultures of PC12 Cells and Sensory Ganglia," *Proc. Natl. Acad. Sci. USA*, 91, pp. 3191–3195 (1994).

W.E. Lyons, et al., "Neuronal Regeneration Enhances the Expression of the Immunophilin FKBP–12," *J. Neuroscience.*, 15, pp. 2985–2994 (Apr., 1995).

(List continued on next page.)

*Primary Examiner*—Mukund J. Shah
*Assistant Examiner*—Deepak R. Rao
*Attorney, Agent, or Firm*—Fish & Neave; James F. Haley, Jr.; N. Govindaswamy

[57] ABSTRACT

The present invention relates to compounds that can maintain, increase, or restore sensitivity of cells to therapeutic or prophylactic agents. This invention also relates to pharmaceutical compositions comprising these compounds. The compounds and pharmaceutical compositions of this invention are particularly well-suited for treatment of multi-drug resistant cells, for prevention of the development of multi-drug resistance, and for use in multi-drug resistant cancer therapy.

16 Claims, No Drawings

OTHER PUBLICATIONS

J. Sharkey and S.P. Butcher, "Immunophilins Mediate the Neuroprotective Effects of FK506 in Focal Cerebral Ischaemia," *Nature,* 371, pp. 336–339 (1994).

J. Steiner, "Neuroimmunophilins and Nerve Regrowth," *Cambridge Healthtech Institute's Alzheimer's Disease: The Promise of New Therapeutics,* Jun. 8, 1995–Jun. 9, 1995.

K. Soai, et. al., "Diastereoselective Reduction of Chiral Alpha–Ketoamides Derived from (S)–Proline Esters with Sodium Borohydride," *J. Chem. Soc. Perkin Trans.* 1, pp. 769–772 (1985).

D.S. Yamashita, et al., "Design, Synthesis and Evaluation of Dual Domain FKBP Ligands," *Bioorg. Med. Chem. Lett.,* 4, pp. 325–328 (1994).

COMPOUNDS WITH IMPROVED MULTI-DRUG RESISTANCE ACTIVITY

This is a division, of application Ser. No. 08/626,259, filed Mar. 29, 1996 entitled Compounds with Improved Multi-Drug Resistance Activity now U.S. Pat. No. 5,717,092.

TECHNICAL FIELD OF THE INVENTION

The present invention relates to novel compounds which can maintain, increase, or restore sensitivity of cells to therapeutic or prophylactic agents. This invention also relates to pharmaceutical compositions comprising these compounds. The compounds and pharmaceutical compositions of this invention are particularly well-suited for treatment of multi-drug resistant cells, for prevention of the development of multi-drug resistance and for use in multi-drug resistant cancer therapy. The present invention also relates to methods and pharmaceutical compositions for stimulating the growth of neurites in nerve cells.

BACKGROUND OF THE INVENTION

A major problem affecting the efficacy of chemotherapy regimens is the evolution of cells which, upon exposure to a chemotherapeutic drug, become resistant to a multitude of structurally unrelated drugs and therapeutic agents. The appearance of such multi-drug resistance often occurs in the presence of overexpression of a 170-KD membrane P-glycoprotein (gp-170 or MDR1). The gp-170 protein is present in the plasma membranes of some healthy tissues, in addition to cancer cell lines, and is homologous to bacterial transport proteins (Hait et al., *Cancer Communications*, Vol. 1(1), 35 (1989); West, *TIBS*, Vol. 15, 42 (1990)). The protein acts as an export pump, conferring drug resistance through active extrusion of toxic chemicals. Although the mechanism for the pump is unknown, it is speculated that the gp-170 protein functions by expelling substances that share certain chemical or physical characteristics, such as hydrophobicity, the presence of carbonyl groups, or the existence of a glutathione conjugate (see West).

Recently, another protein responsible for multidrug resistance, MRP (multidrug resistance associated protein), was identified in H69AR cells, an MDR cell line that lacks detectable P-glycoprotein [S. P. C. Cole et al., *Science*, 258, pp. 1650–54 (1992)]. MRP has also been detected in other non-P-glycoprotein MDR cell lines, such as HL60/ADR and MCF-7 breast carcinoma cells [(E. Schneider et al., *Cancer Ret.*, 54, pp. 152–58 (1994); and N. Krishnamachary et al., *Cancer Res.*, 53, pp. 3658–61 (1993)].

The MRP gene encodes a 190 KD membrane-associated protein that is another member of the ATP binding cassette superfamily. MRP appears to function in the same manner as P-glycoprotein, acting as a pump for removing natural product drugs from the cell. A possible physiological function for MRP may be ATP-dependent transport of glutathione S-conjugates [G. Jedlitschky et al., *Cancer Res.*, 54, pp. 4833–36 (1994); I. Leier et al., *J. Biol. Chem.*, 269, pp. 27807–10 (1994); and Muller et al., *Proc. Natl. Acad. Sci. USA*, 91, pp. 13033–37 (1994)].

The role of MRP in clinical drug resistance remains to be clearly defined, but it appears likely that MRP may be another protein responsible for a broad resistance to anti-cancer drugs.

Various chemical agents have been administered to repress multi-drug resistance and restore drug sensitivity. While some drugs have improved the responsiveness of multi-drug resistant ("MDR") cells to chemotherapeutic agents, they have often been accompanied by undesirable clinical side effects (see Hait et al.). For example, although cyclosporin A ("CsA"), a widely accepted immunosuppressant, can sensitize certain carcinoma cells to chemotherapeutic agents (Slater et al., *Br. J. Cancer*, Vol. 54, 235 (1986)), the concentrations needed to achieve that effect produce significant immunosuppression in patients whose immune systems are already compromised by chemotherapy (see Hait et al.). In addition, CsA usage is often accompanied by adverse side effects including nephrotoxicity, hepatotoxicity and central nervous system disorders. Similarly, calcium transport blockers and calmodulin inhibitors both sensitize MDR cells, but each produces undesirable physiological effects (see Hait et al.; Twentyman et al., *Br. J. Cancer*, Vol. 56, 55 (1987)).

Recently, agents have been developed which may be of potentially greater clinical value in the sensitization of MDR cells. These agents include analogs of CsA which do not exert an immunosuppressive effect, such as 11-methyl-leucine cyclosporin (11-met-leu CsA) (see Hait et al.; Twentyman et al.), or agents that may be effective at low doses, such as the immunosuppressant FK-506 (Epand and Epand, *Anti-Cancer Drug Design* 6, 189 (1991)). PCT publication WO 94/07858 refers to a novel class of MDR modifying agents with some structural similarities to the immunophilins FK-506 and rapamycin. Despite these developments, there is still a need for more effective agents which may be used to resensitize MDR cells to therapeutic or prophylactic agents or to prevent the development of multi-drug resistance.

Interestingly, compounds such as the immunophilin FK506 have been shown to not only be effective against multi-drug resistance, but also to be effective in stimulating neurite outgrowth. In co-pending U.S. patent application Ser. No. 08/486,004, a co-applicant of the present invention discovered that other MDR reversing compounds could also stimulate neurite outgrowth in the presence or absence of exogenous or endogenous NGF. These compounds all had the ability to bind the cellular protein FKBP12. FKBP12 appears to be linked to neurite outgrowth because expression of FKBP12 alone has been found to stimulate neurite outgrowth in nerve cells.

W. E. Lyons et al. [*Proc. Natl. Acad. Sci. USA*, 91, pp. 3191–95 (1994)] demonstrated FK506 acts synergistically nerve growth factor (NGF) in stimulating neurite outgrowth in a rat pheochromocytoma cell line. Interestingly, another immunophilin, rapamycin, did not inhibit the effects of FK-506 on neurite outgrowth, but rather was neurotrophic itself, displaying an additive effect with FK-506. In sensory ganglia, FK-506 demonstrated similar neurotrophic effects, but those effects were blocked by rapamycin. Both rapamycin and FK506 have the ability to bind to a cellular protein, FK506 binding protein or FKBP12.

These results led the authors to speculate that FK-506 was exerting its neurotrophic effect through its complexing with FKBP12 and calcineurin and inhibition of the latter's phosphatase activity. Alternatively, the authors proposed FK-506 was acting via a "stripping" mechanism, such as that involved in the removal of FKBP12 from membrane receptors, RyR and $IP_3R$.

In view of the wide variety of disorders that may be treated by stimulating neurite outgrowth and the relatively few FKBP12-binding compounds that are known to possess this property, there remains a great need for additional neurotrophic, FKBP12-binding compounds.

SUMMARY OF THE INVENTION

The present invention provides novel compounds that have a surprisingly improved ability, as compared with previously described MDR modifiers, to maintain, increase or restore drug sensitivity in multi-drug resistant ("MDR") cells, compositions containing these compounds and methods for using them. The compounds of this invention may be used alone or in combination with other therapeutic or prophylactic agents to maintain, increase or restore the therapeutic or prophylactic effects of drugs in cells, especially MDR cells, or to prevent the development of MDR cells. According to one embodiment of this invention, these novel compounds, compositions and methods are advantageously used to aid or enhance chemotherapy regimens for the treatment or prophylaxis of cancer and other diseases. The present invention also provides methods for preparing the compounds of this invention and intermediates useful in those methods.

In another embodiment, the present invention also relates to methods and pharmaceutical compositions for stimulating the growth of neurites in nerve cells. The compounds of this invention bind FKBP12 and cause a significant increase in neurite outgrowth.

The neurotrophic compositions provided comprise a compound of this invention alone or together with a known neurotrophic factor. The methods described herein employ those compositions to effectuate neurite outgrowth and are thus useful to treat nerve damage caused by various diseases and physical traumas.

DETAILED DESCRIPTION OF THE INVENTION

This invention relates to two related classes of compounds which have the ability either to increase toxicity of drugs in multi-drug resistant (MDR) cells and to stimulate neurite outgrowth in nerve cells. One of these classes of compounds is represented by formula (I):

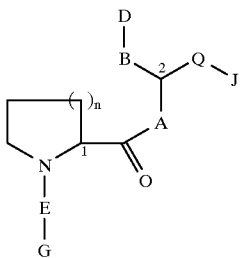

wherein:

A is $CH_2$, O, NH or N—[(C1–C4)-alkyl];

B is (C1–C6)-straight or branched alkyl, or (C2–C6)-straight or branched alkenyl or alkynyl, wherein one of the carbon atoms of B is optionally replaced by O, S, SO, $SO_2$, NH or N—[(C1–C4)-alkyl];

D is 1-[(C1–C4)-alkyl]-4-piperidinyl; 1-piperazinyl; 1-[(C1–C4)-alkyl]-4-piperazinyl; a 5–7-membered cycloalkyl or cycloalkenyl ring optionally comprising substituents at the 3 and/or 4 position of said ring, wherein said substituents are selected from oxo, OH, (C1–C4)-alkyl, O—[(C1–C4)-alkyl], O—[(C2–C4)-alkenyl], $NH_2$, N,N di-[(C1–C4)-alkyl] amino or halogen; or a monocyclic or bicyclic aromatic ring structure consisting of 5 to 6 members in each ring and optionally comprising up to 4 heteroatoms independently selected from N, O or S;

E is $SO_2$ or —C(O)—C(O)—;

G is 1-[(C1–C4)-alkyl]-4-piperidinyl, 1-piperazinyl, 1-[(C1–C4)-alkyl]-4-piperazinyl, (C1–C7)-straight or branched alkyl, (C2–C7)-straight or branched alkenyl or alkynyl, (C5–C7)-cycloalkyl, or a monocyclic or bicyclic aromatic ring structure consisting of 5 to 6 members in each ring; wherein up to two carbon atoms in any G are optionally replaced independently by O, S, SO, $SO_2$ or N;

wherein G optionally comprises up to three substituents independently selected from halogen, hydroxyl, (C1–C6)-straight or branched alkyl, (C2–C6)-straight or branched alkenyl, O—[(C1–C5)-straight or branched alkyl], O—[(C2–C5)-straight or branched alkenyl], O-benzyl, amino, carboxyl, N—[(C1–C5)-straight or branched alkyl], N—[(C2–C5)-straight or branched alkenyl], trifluoromethyl or trifluoromethoxy; and wherein one carbon atom of any individual substituent is optionally replaced by O, N or S;

Q is a five membered aromatic ring containing 1 to 2 heteroatoms selected from N, O or S, or a six membered aromatic ring containing 0 to 2 heteroatoms selected from N, O or S;

J is a monocyclic or bicyclic aromatic ring structure attached to the 3 position of Q consisting of 5 to 6 members in each ring, optionally comprising up to four heteroatoms independently selected from O, S, or N; and wherein J optionally comprises up to 3 substituents independently selected from halo, OH, $CH_2OH$, $NO_2$, $SO_3H$, trifluoromethyl, trifluoromethoxy, O-phenyl, 1,2-methylenedioxy, $NR^1R^2$, amino, carboxyl, N—[(C1–C5)-straight or branched alkyl]-carboxamide, N—[(C2–C5)-straight or branched alkenyl]-carboxamide, N-morpholinocarboxamide, N-benzylcarboxamide, N-thiomorpholinocarboxamide, N-picolinoylcarboxamide, morpholinyl, piperidinyl, O—$R^3$, $CH_2$—$(CH_2)_q$—$R^3$, O—$(CH_2)_q$—$R^3$, $(CH_2)_q$—O—$R^3$, CH=CH—$R^3$, (C1–C6)-straight or branched alkyl, or (C2–C6)-straight or branched alkenyl, wherein in any substituent one carbon atom is optionally replaced by a heteroatom selected from the group consisting of O, S, SO, $SO_2$, NH or N—[(C1–C4)-alkyl];

wherein $R^1$ and $R^2$ are independently selected from the group consisting of hydrogen, (C1–C6)-straight or branched alkyl, (C2–C6)-straight or branched alkenyl or alkynyl and benzyl;

$R^3$ is selected from the group consisting of 4-methoxyphenyl, 2-pyridyl, 3-pyridyl, 4-pyridyl, pyrazyl, quinolyl, 3,5-dimethylisoxazoyl, 2-methylthiazoyl, thiazoyl, 2-thienyl, 3-thienyl and pyrimidyl; and q is 0–2; and n is 1 or 2.

The "3 position of Q" recited above is relative to the point of attachment of Q to the rest of the compound. For the purposes of this application, this point of attachment is designated the 1 position, regardless of any potential conflict with accepted chemical nomenclature.

The term "carbon atom", as used herein in reference to something that is "optionally replaced by" O, S, SO, $SO_2$, NH or N—[(C1–C4)-alkyl], includes C, CH, $CH_2$ or $CH_3$, depending upon where in an alkyl, alkenyl, alkynyl, cycloalkyl or cycloalkenyl chain or ring that carbon atom is located. Similarly, the reference to replacement by O, S, SO, $SO_2$, NH or N—[(C1–C4)-alkyl] includes O, OH, S, SH, $SH_2$, SO, SOH, N, NH, $NH_2$, N—[(C1–C4)-alkyl] and N(H)—[(C1–C4)-alkyl], again depending upon the location of the replacement in the chain or ring.

The other class of compounds of this invention are represented by formula (II):

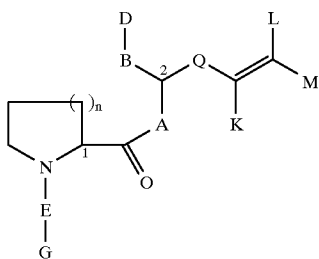

wherein:

A, B, D, E, G and Q are as defined as above;

K is H, (C5–C7) cycloalkyl, (C5–C6) aromatic ring, 1-[(C1–C4)-alkyl]-4-piperidinyl, 1-piperazinyl, 1-[(C1–C4)-alkyl]-4-piperazinyl, (C1–C7)-straight or branched alkyl, (C2–C7)-straight or branched alkenyl or alkynyl, wherein up to two carbon atoms in K are optionally replaced independently by O, S, SO, $SO_2$, NH, NO or N—(C1–C4)-alkyl, wherein K optionally comprises up to 2 substituents independently selected from halo, amino, hydroxy, carboxy, methoxy or (C1–C3)alkyl; and L and M are independently selected from H, (C1–C7)-straight or branched alkyl, (C2–C7)-straight or branched alkenyl or alkynyl, wherein one carbon atom in $R^2$ and $R^3$ is optionally replaced by O, S, SO, $SO_2$ NH or N—(C1–C4)-alkyl, wherein L and M optionally comprise up to two substituents independently selected from halogen, hydroxy, amino, carboxy, or a 5 to 6 membered aromatic ring, said aromatic ring comprising up to two heteroatoms selected from N, O or S; and n is 1 or 2.

Compounds of formulae (I) and (II) of this invention include all optical and racemic isomers. The stereochemistry at positions 1 and 2 may be either R or S. In a preferred embodiment, the stereochemistry at position 1 is S.

Preferably, none of the monocyclic or bicyclic rings that may be present in either compounds of formulae (I) or (II) contain more than one heteroatom per ring.

More preferably, in compounds of formulae (I) and (II), A is oxygen and E is —C(O)—C(O)—. Even more preferred are compounds wherein n is 2 and the potential location of heteroatoms in Q exclude the 1 and 3 positions (i.e., the position where the aromatic ring is bound to the rest of the molecule and the position where J is bound to the aromatic ring). These compounds are represented by formulae (III) and (IV):

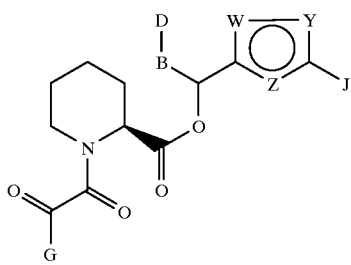

(III)

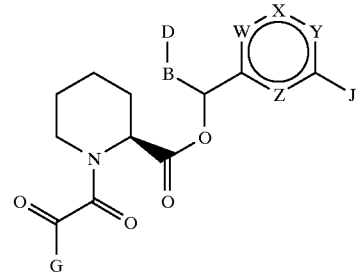

(IV)

Preferably in compounds of formulae (III) and (IV):

B is propyl, ethyl, or 1-methylethenyl;

D is phenyl, N-morpholinyl, 4-hydroxy-cyclohexyl, 4-(N-methyl)-piperidinyl, 4-pyridyl or pyranyl;

G is 3,4,5-trimethoxyphenyl, 3,4-dimethoxyphenyl, 4-fluorophenyl, 2-furanyl, 1,1-dimethyl-2-methoxyethyl, t-butyl, 4-(4-hydroxy) pyranyl, isobutyl, 4-pyranyl, isobutyl, isopropyl, 1-methylcyclohexyl, 1,1,2-trimethylpropyl, 1-hydroxycyclohexyl, 1-trimethylpropyl, 4-methoxy-1-hydroxy-cyclohexyl, 5-methoxymethyl-2-methylphenyl, 2-methylcyclohexyl, 5-(1-methyl-1-methoxyethyl)-2-methylcyclohexyl-2-enyl, 2-methylcyclohexyl, 5-(1-methyl-1-methoxyethyl)-2-methylcyclohexyl, 5-ethoxy-2-methylcyclohexyl, 4-ethoxy-N-aceto-2-pyrrolidinyl, or 5-isopropyl-2-methylcyclohexyl; and J is 4-phenyl-1-(3-pyridyl)-1-butenyl, 2,5-diethoxyphenyl, 4-phenyl-1-(3-pyridyl-N-oxide)-1-butenyl, 2-methoxyphenyl, 1-(3-pyridyl)-1-pentenyl, 2-ethoxyphenyl, 2,5-dipropoxyphenyl, 2,6-dimethoxyphenyl, 1-(3-pyridyl)-1-butenyl, 1-(3-pyridyl)-1-pentenyl, 1-(3-pyridyl)-1-hexenyl, 1-(4-methylphenyl)-1-pentenyl, 2,6-dimethoxymethylphenyl, 1-cyclohexyl-1-pentenyl, 2-ethoxymethyl-N-indolyl, 1-cyclohexyl-3-methoxy-1-propenyl, 2,6-diethoxymethylphenyl, 1-(3-pyridyl)-1-hexa-1,5-dienyl, 1-(4-pyranyl)-1-hexa-1,5-dienyl, 1-cyclohexyl-1-hexenyl, 2,5-dipropyl-N-pyrrolyl, 2-methyl-5-butyl-N-pyrrolyl, 3-(1-methoxy)-2-hexenyl, 3-(1-methoxy)-4-methyl-2-pentenyl, 2,5-dimethyl-N-pyrrolyl, 3-(2-methyl)-3-heptenyl or 2-(2-hexenyl); and W, X, Y and Z are independently selected from CH, N, O or S.

The most preferred compounds of this invention are represented by formulae (III) and (IV) with the other components and the orientation ("R/S") listed in the table below. Compounds of formula (III) are distinguished from those of formula (IV) by the lack of a "W" component (indicated by a "–" in the table).

| # | B | D | G | J | W | X | Y | Z | R/S |
|---|---|---|---|---|---|---|---|---|---|
| 3 | propyl | phenyl | 3,4,5-trimethoxyphenyl | 2,4-phenyl-1-(3-pyridyl)-1-butenyl | CH | CH | CH | CH | R/S |
| 4 | propyl | phenyl | 3,4,5-trimethoxyphenyl | 2,5-diethoxyphenyl | CH | CH | CH | CH | R/S |
| 5 | propyl | phenyl | 3,4,5-trimethoxyphenyl | E-4-phenyl-1-(3-pyridyl)-1-butenyl | CH | CH | CH | CH | S |
| 6 | propyl | phenyl | 3,4,5-trimethoxyphenyl | E-4-phenyl-1-(3-pyridyl)-1-butenyl | CH | CH | CH | CH | R |
| 7 | propyl | phenyl | 3,4,5-trimethoxyphenyl | 2,5-diethoxyphenyl | CH | CH | CH | CH | S |
| 8 | propyl | phenyl | 3,4,5-trimethoxyphenyl | 2,5-diethoxyphenyl | CH | CH | CH | CH | R |
| 9 | propyl | phenyl | 3,4,5-trimethoxyphenyl | E-4-phenyl-1-(3-pyridyl-N-oxide)-1-butenyl | CH | CH | CH | CH | R |
| 10 | propyl | phenyl | 3,4,5-trimethoxyphenyl | 2,5-diethoxyphenyl | CH | N | CH | CH | R |
| 11 | propyl | phenyl | 3,4-dimethoxyphenyl | 2,5-diethoxyphenyl | CH | N | CH | CH | R |
| 12 | propyl | phenyl | 3,4-dimethoxyphenyl | 2,5-diethoxyphenyl | CH | N | CH | CH | S |
| 13 | propyl | phenyl | 3,4-dimethoxyphenyl | 2-methoxyphenyl | CH | N | CH | CH | R |
| 14 | propyl | phenyl | 3,4-dimethoxyphenyl | 2-methoxyphenyl | CH | N | CH | CH | S |
| 15 | propyl | phenyl | 3,4,5-trimethoxyphenyl | 2-methoxyphenyl | CH | N | CH | CH | R |
| 16 | propyl | phenyl | 3,4,5-trimethoxyphenyl | E-1-(3-pyridyl)-1-pentenyl | CH | CH | CH | CH | S |
| 17 | propyl | phenyl | 3,4,5-trimethoxyphenyl | E-1-(3-pyridyl)-1-pentenyl | CH | CH | CH | CH | R |
| 18 | propyl | phenyl | 3,4,5-trimethoxyphenyl | 2-ethoxyphenyl | CH | N | CH | CH | R |
| 19 | propyl | phenyl | 3,4,5-trimethoxyphenyl | 2-ethoxyphenyl | CH | N | CH | CH | S |
| 20 | propyl | phenyl | 3,4-dimethoxyphenyl | 2-ethoxyphenyl | CH | N | CH | CH | R |
| 21 | propyl | phenyl | 3,4-dimethoxyphenyl | 2-ethoxyphenyl | CH | N | CH | CH | S |
| 22 | propyl | phenyl | 3,4,5-trimethoxyphenyl | 2,5-dipropoxyphenyl | CH | N | CH | CH | R |
| 23 | propyl | phenyl | 3,4,5-trimethoxyphenyl | 2,5-dipropoxyphenyl | CH | N | CH | CH | S |
| 24 | propyl | phenyl | 3,4,5-trimethoxyphenyl | 2,6-dimethoxyphenyl | CH | N | CH | CH | R |
| 25 | propyl | phenyl | 3,4,5-trimethoxyphenyl | 2,6-dimethoxyphenyl | CH | N | CH | CH | S |
| 26 | ethyl | N-morpholinyl | 3,4,5-trimethoxyphenyl | E-1-(3-pyridyl)-1-pentenyl | CH | CH | CH | CH | R |
| 27 | ethyl | N-morpholinyl | 3,4,5-trimethoxyphenyl | E-1-(3-pyridyl)-1-pentenyl | CH | CH | CH | CH | S |
| 28 | propyl | phenyl | 3,4,5-trimethoxyphenyl | E-1-(3-pyridyl)-1-butenyl | CH | CH | CH | CH | S |
| 29 | propyl | phenyl | 3,4,5-trimethoxyphenyl | E-1-(3-pyridyl)-1-butenyl | CH | CH | CH | CH | R |
| 30 | ethyl | N-morpholinyl | 3,4,5-trimethoxyphenyl | Z-1-(3-pyridyl)-1-pentenyl | CH | CH | CH | CH | R |
| 31 | ethyl | N-morpholinyl | 3,4,5-trimethoxyphenyl | Z-1-(3-pyridyl)-1-pentenyl | CH | CH | CH | CH | S |
| 32 | E-(1-methyl)ethenyl | trans-4-hydroxy-cyclohexyl | 3,4,5-trimethoxyphenyl | 2,6-dimethoxyphenyl | CH | N | CH | CH | R |
| 33 | E-(1-methyl)ethenyl | trans-4-hydroxy-cyclohexyl | 3,4,5-trimethoxyphenyl | 2,6-dimethoxyphenyl | CH | N | CH | CH | S |
| 34 | ethyl | N-morpholinyl | 3,4,5-trimethoxyphenyl | E-1-(3-pyridyl)-1-hexenyl | CH | CH | CH | CH | R |
| 35 | ethyl | N-morpholinyl | 3,4,5-trimethoxyphenyl | E-1-(3-pyridyl)-1-hexenyl | CH | CH | CH | CH | S |
| 36 | propyl | phenyl | 3,4,5-trimethoxyphenyl | E-1-(3-pyridyl)-1-hexenyl | CH | CH | CH | CH | S |
| 37 | propyl | phenyl | 3,4,5-trimethoxyphenyl | E-1-(3-pyridyl)-1-hexenyl | CH | CH | CH | CH | R |
| 38 | E-(1-methyl)ethenyl | trans-4-hydroxy-cyclohexyl | 4-fluorophenyl | Z-1-(4-methylphenyl)-1-pentenyl | CH | N | CH | CH | S |

-continued

| # | B | D | G | J | W | X | Y | Z | R/S |
|---|---|---|---|---|---|---|---|---|---|
| 39 | E-(1-methyl)ethenyl | trans-4-hydroxy-cyclohexyl | 4-fluorophenyl | Z-1-(4-methylphenyl)-1-pentenyl | CH | N | CH | CH | R |
| 40 | E-(1-methyl)ethenyl | trans-4-hydroxy-cyclohexyl | 2-furanyl | 2,6-dimethoxymethyl phenyl | CH | N | CH | CH | S |
| 41 | E-(1-methyl)ethenyl | trans-4-hydroxy-cyclohexyl | 2-furanyl | 2,6-dimethoxymethyl phenyl | CH | N | CH | CH | R |
| 42 | E-(1-methyl)ethenyl | trans-4-hydroxy-cyclohexyl | 4-fluorophenyl | Z-1-cyclohexyl-1-pentenyl | CH | N | CH | CH | S |
| 43 | E-(1-methyl)ethenyl | trans-4-hydroxy-cyclohexyl | 2-furanyl | 2-ethoxymethyl-N-indolyl | CH | CH | CH | CH | S |
| 44 | E-(1-methyl)ethenyl | trans-4-hydroxy-cyclohexyl | 2-furanyl | 2-ethoxymethyl-N-indolyl | CH | CH | CH | CH | R |
| 45 | E-(1-methyl)ethenyl | trans-4-hydroxy-cyclohexyl | 2-furanyl | Z-1-cyclohexyl-1-pentenyl | CH | N | CH | CH | S |
| 46 | E-(1-methyl)ethenyl | trans-4-hydroxy-cyclohexyl | 2-furanyl | Z-1-cyclohexyl-1-pentenyl | CH | N | CH | CH | R |
| 47 | E-(1-methyl)ethenyl | trans-4-hydroxy-cyclohexyl | 2-furanyl | Z-1-cyclohexyl-1-methoxy-propenyl | CH | N | CH | CH | R |
| 48 | E-(1-methyl)ethenyl | trans-4-hydroxy-cyclohexyl | 2-furanyl | Z-1-cyclohexyl-1-methoxy-propenyl | CH | N | CH | CH | S |
| 49 | ethyl | N-morpholinyl | 1,1-dimethyl-2-methoxyethyl | 2,6-diethoxymethyl phenyl | — | S | CH | CH | ND |
| 50 | ethyl | N-morpholinyl | 1,1-dimethyl-2-methoxyethyl | 2,6-diethoxymethyl phenyl | — | S | CH | CH | ND |
| 51 | E-(1-methyl)ethenyl | trans-4-hydroxy-cyclohexyl | 1,1-dimethyl-2-methoxyethyl | 2,6-dimethoxymethyl phenyl | CH | N | CH | CH | R |
| 52 | E-(1-methyl)ethenyl | 4-(N-methyl)-piperidinyl | t-butyl | Z-1-(3-pyridyl)-1-hexa-1,5-dienyl | — | CH | CH | S | S |
| 53 | E-(1-methyl)ethenyl | 4-(N-methyl)-piperidinyl | t-butyl | Z-1-(3-pyridyl)-1-hexa-1,5-dienyl | — | CH | CH | S | R |
| 54 | E-(1-methyl)ethenyl | trans-4-hydroxy-cyclohexyl | 1,1-dimethyl-2-methoxyethyl | 2-ethoxymethyl-N-indolyl | CH | CH | CH | CH | R |
| 55 | E-(1-methyl)ethenyl | 4-(N-methyl)-piperidinyl | 1,1-dimethyl-2-methoxyethyl | Z-1-(3-pyridyl)-1-hexa-1,5-dienyl | — | CH | CH | S | S |
| 56 | E-(1-methyl)ethenyl | 4-(N-methyl)-piperidinyl | 1,1-dimethyl-2-methoxyethyl | Z-1-(3-pyridyl)-1-hexa-1,5-dienyl | — | CH | CH | S | R |
| 57 | E-(1-methyl)ethenyl | trans-4-hydroxy-cyclohexyl | 4-(4-hydroxy)pyranyl | 2-ethoxymethyl-N-indolyl | CH | CH | CH | CH | R |
| 58 | E-(1-methyl)ethenyl | trans-4-hydroxy-cyclohexyl | 1,1-dimethyl-2-methoxyethyl | 2-ethoxymethyl-N-indolyl | CH | CH | CH | CH | R |
| 59 | E-(1-methyl)ethenyl | trans-4-hydroxy-cyclohexyl | isobutyl | Z-1-cyclohexyl-3-methoxy-1-propenyl | CH | N | CH | CH | S |
| 60 | E-(1-methyl)ethenyl | trans-4-hydroxy-cyclohexyl | isobutyl | Z-1-cyclohexyl-3-methoxy-1-propenyl | CH | N | CH | CH | R |
| 61 | ethyl | N-morpholinyl | 4-pyranyl | 2,6-diethoxymethyl phenyl | — | S | CH | CH | S |
| 62 | ethyl | N-morpholinyl | t-butyl | 2,6-diethoxymethyl phenyl | — | S | CH | CH | R |
| 63 | ethyl | N-morpholinyl | t-butyl | 2,6-diethoxymethyl phenyl | — | S | CH | CH | R |
| 64 | ethyl | N-morpholinyl | t-butyl | 2,6-diethoxymethyl phenyl | — | S | CH | CH | S |
| 65 | E-(1-methyl)ethenyl | trans-4-hydroxy-cyclohexyl | 4-(4-hydroxy)pyranyl | 2-ethoxymethyl-N-indolyl | CH | CH | CH | CH | R |
| 66 | ethyl | N-morpholinyl | isobutyl | Z-1-(4-pyranyl)-1-hexa-1,5-dienyl | — | CH | CH | S | R |

-continued

| #  | B | D | G | J | W | X | Y | Z | R/S |
|----|---|---|---|---|---|---|---|---|-----|
| 67 | E-(1-methyl)ethenyl | 4-pyridyl | t-butyl | 2,6-diethoxymethyl phenyl | CH | N | CH | CH | R/S |
| 68 | E-(1-methyl)ethenyl | 4-pyridyl | 4-pyranyl | 2,6-diethoxymethyl phenyl | CH | N | CH | CH | R/S |
| 69 | ethyl | N-morpholinyl | isobutyl | Z-1-(4-pyranyl)-1-hexa-1,5-dienyl | — | CH | CH | S | S |
| 70 | ethyl | N-morpholinyl | t-butyl | Z-1-(4-pyranyl)-1-hexa-1,5-dienyl | — | CH | CH | S | R |
| 71 | E-(1-methyl)ethenyl | 4-(N-methyl)-piperidinyl | isobutyl | Z-1-(3-pyridyl)-1-hexa-1,5-dienyl | — | CH | CH | S | S |
| 72 | E-(1-methyl)ethenyl | 4-(N-methyl)-piperidinyl | isobutyl | Z-1-(3-pyridyl)-1-hexa-1,5-dienyl | — | CH | CH | S | R |
| 73 | ethyl | N-morpholinyl | isobutyl | 2,6-diethoxymethyl phenyl | CH | N | CH | CH | R |
| 74 | E-(1-methyl)ethenyl | 4-(N-methyl)-piperidinyl | isopropyl | Z-1-cyclohexyl-1-hexenyl | CH | N | CH | CH | S |
| 75 | E-(1-methyl)ethenyl | 4-(N-methyl)-piperidinyl | isopropyl | Z-1-cyclohexyl-1-hexenyl | CH | N | CH | CH | R |
| 76 | ethyl | N-morpholinyl | 1-methylcyclohexyl | 2,6-diethoxymethyl phenyl | CH | N | CH | CH | S |
| 77 | ethyl | N-morpholinyl | isobutyl | 2,6-diethoxymethyl phenyl | CH | N | CH | CH | S |
| 78 | ethyl | N-morpholinyl | 1-methylcyclohexyl | 2,6-diethoxymethyl phenyl | CH | N | CH | CH | R |
| 79 | ethyl | N-morpholinyl | 1-methylcyclohexyl | 2,6-diethoxymethyl phenyl | CH | N | CH | CH | R |
| 80 | ethyl | N-morpholinyl | 1-methylcyclohexyl | 2,6-diethoxymethyl phenyl | CH | N | CH | CH | S |
| 81 | ethyl | N-morpholinyl | t-butyl | 2,6-diethoxymethyl phenyl | CH | N | CH | CH | R |
| 82 | ethyl | N-morpholinyl | t-butyl | 2-ethoxymethyl-N-indolyl | CH | CH | CH | CH | R |
| 83 | ethyl | N-morpholinyl | isobutyl | 2,6-diethoxymethyl phenyl | — | CH | CH | S | R |
| 84 | ethyl | N-morpholinyl | isobutyl | 2,6-diethoxymethyl phenyl | — | CH | CH | S | S |
| 85 | ethyl | N-morpholinyl | 1-methylcyclohexyl | Z-1-(3-pyridyl)-1-hexa-1,5-dienyl | — | CH | CH | S | R |
| 86 | ethyl | N-morpholinyl | 1-methylcyclohexyl | 2-ethoxymethyl-N-indolyl | CH | CH | CH | CH | R |
| 87 | ethyl | N-morpholinyl | 1-methylcyclohexyl | Z-1-(4-pyranyl)-1-hexa-1,5-dienyl | — | CH | CH | S | S |
| 88 | propyl | phenyl | 3,4,5-trimethoxyphenyl | 2,5-diethoxyphenyl | CH | N | CH | CH | S |
| 89 | ethyl | N-morpholinyl | 1,1,2-trimethylpropyl | 2,6-diethoxymethyl phenyl | CH | N | CH | CH | ND |
| 90 | ethyl | N-morpholinyl | 1,1,2-trimethylpropyl | Z-1-(3-pyridyl)-1-hexa-1,5-dienyl | — | CH | CH | S | ND |
| 91 | ethyl | N-morpholinyl | 1,1,2-trimethylpropyl | Z-1-(4-pyranyl)-1-hexa-1,5-dienyl | — | CH | CH | S | ND |
| 92 | ethyl | N-morpholinyl | 1,1,2-trimethylpropyl | E-1-(3-pyridyl)-1-pentenyl | CH | CH | CH | CH | ND |
| 93 | ethyl | N-morpholinyl | 1,1,2-trimethylpropyl | 2,6-diethoxymethyl phenyl | — | CH | CH | S | R |
| 94 | ethyl | N-morpholinyl | 1,1,2-trimethylpropyl | 2-ethoxymethyl-N-indolyl | CH | CH | CH | CH | R |
| 95 | ethyl | N-morpholinyl | 1-hydroxy-cyclohexyl | Z-1-(4-pyranyl)-1-hexa-1,5-dienyl | — | CH | CH | S | R |
| 96 | ethyl | N-morpholinyl | 1-methylcyclohexyl | Z-1-(3-pyridyl)-1-hexa-1,5-dienyl | — | CH | CH | S | R |
| 97 | ethyl | N-morpholinyl | t-butyl | 2-ethoxymethyl-N-indolyl | CH | CH | CH | CH | R |
| 98 | E-(1-methyl ethenyl) | 4-pyridyl | 1,1,2-trimethylpropyl | Z-1-cyclohexyl-1-pentenyl | CH | N | CH | CH | R |
| 99 | E-(1-methyl ethenyl) | 4-pyridyl | cis-(4-methoxy-1-hydroxyl cyclohexyl | Z-1-cyclohexyl-1-pentenyl | CH | N | CH | CH | ND |
| 100 | E-(1-methyl ethenyl) | 4-pyridyl | cis-(4-methoxy-1-hydroxyl cyclohexyl | Z-1-cyclohexyl-1-pentenyl | CH | N | CH | CH | ND |

-continued

| # | B | D | G | J | W | X | Y | Z | R/S |
|---|---|---|---|---|---|---|---|---|---|
| 101 | ethyl | N-morpholinyl | 5-methoxymethyl-2-methylphenyl | Z-1-(3-pyridyl)-1-hexa-1,5-dienyl | — | CH | CH | S | S |
| 102 | ethyl | N-morpholinyl | 5-methoxymethyl-2-methylphenyl | 2,6-diethoxymethylphenyl | — | CH | CH | S | R |
| 103 | ethyl | N-morpholinyl | 1,1,2-trimethylpropyl | 2,5-dipropyl-N-pyrrolyl | CH | CH | CH | CH | R |
| 104 | ethyl | N-morpholinyl | 1,1,2-trimethylpropyl | 2,5-dipropyl-N-pyrrolyl | CH | CH | CH | CH | S |
| 105 | ethyl | N-morpholinyl | (1R, 2R)-2-methylcyclohexyl | 2,5-dipropyl-N-pyrrolyl | CH | CH | CH | CH | R |
| 106 | E-(1-methyl)ethenyl | 4-pyridyl | 1,1,2-trimethylpropyl | 2,5-dipropyl-N-pyrrolyl | CH | CH | CH | CH | R |
| 107 | ethyl | N-morpholinyl | (R,R-)-5-(1-methyl-1-methoxyethyl)-2-methylcyclohexyl-2-enyl | 2,5-dipropyl-N-pyrrolyl | CH | CH | CH | CH | R |
| 108 | E-(1-methyl)ethenyl | 4-pyridyl | (1R, 2R)-2-methylcyclohexyl | 2,5-dipropyl-N-pyrrolyl | CH | CH | CH | CH | ND |
| 109 | E-(1-methyl)ethenyl | 4-pyridyl | 1,1,2-trimethylpropyl | 2,5-dipropyl-N-pyrrolyl | CH | CH | CH | CH | ND |
| 110 | ethyl | N-morpholinyl | (R,R,R)-5-(1-methyl-1-methoxyethyl)-2-methylcyclohexyl | 2,5-dipropyl-N-pyrrolyl | CH | CH | CH | CH | R |
| 111 | ethyl | N-morpholinyl | (R,R,R)-5-ethoxy-2-methylcyclohexyl | 2,5-dipropyl-N-pyrrolyl | CH | CH | CH | CH | R |
| 112 | ethyl | N-morpholinyl | (R,R,R)-5-(1-methyl-1-methoxyethyl)-2-methylcyclohexyl | 2-methyl-5-butyl-N-pyrrolyl | CH | CH | CH | CH | R |
| 113 | ethyl | N-morpholinyl | 1,1,2-trimethylpropyl | Z-3-(1-methoxy)-2-hexenyl | CH | N | CH | CH | R |
| 114 | ethyl | N-morpholinyl | 1,1,2-trimethylpropyl | Z-3-(1-methoxy)-2-hexenyl | CH | N | CH | CH | S |
| 115 | ethyl | N-morpholinyl | 1,1,2-trimethylpropyl | Z-3-(1-methoxy)-4-methyl-2-pentenyl | CH | N | CH | CH | R |
| 116 | ethyl | N-morpholinyl | 1,1,2-trimethylpropyl | Z-3-(1-methoxy)-4-methyl-2-pentenyl | CH | N | CH | CH | S |
| 117 | ethyl | N-morpholinyl | (1R, 2R)-2-methylcyclohexyl | Z-3-(1-methoxy)-2-hexenyl | CH | N | CH | CH | R |
| 118 | ethyl | N-morpholinyl | (1R, 2R)-2-methylcyclohexyl | Z-3-(1-methoxy)-2-methyl-2-pentenyl | CH | N | CH | CH | R |
| 119 | ethyl | N-morpholinyl | (2S, 4R)-4-ethoxy-N-aceto-2-pyrrolidinyl | Z-3-(1-methoxy)-4-hexenyl | CH | N | CH | CH | R |
| 120 | ethyl | N-morpholinyl | (1R, 2R)-2-methylcyclohexyl | 2-methyl-5-butyl-N-pyrrolyl | CH | CH | CH | CH | R |
| 121 | ethyl | N-morpholinyl | (R,R,R)-5-ethoxy-2-methylcyclohexyl | 2-methyl-5-butyl-N-pyrrolyl | CH | CH | CH | CH | R |
| 122 | ethyl | N-morpholinyl | 1,1,2-trimethylpropyl | 2-methyl-5-butyl-N-pyrrolyl | CH | CH | CH | CH | R |
| 123 | ethyl | N-morpholinyl | (R,R,R)-5-(1-methyl-1-methoxyethyl)-2-methylcyclohexyl | Z-3-(1-methoxy)-2-hexenyl | CH | N | CH | CH | R |
| 124 | ethyl | N-morpholinyl | (R,R,R)-5-(1-methyl-1-methoxyethyl)-2-methylcyclohexyl | Z-3-(1-methoxy)-4-methyl-2-pentenyl | CH | N | CH | CH | R |
| 125 | ethyl | N-morpholinyl | (R,R,R)-5-ethoxy-2-methylcyclohexyl | Z-3-(1-methoxy)-2-hexenyl | CH | N | CH | CH | ND |
| 126 | ethyl | N-morpholinyl | (R,R,R)-5-isopropyl-2-methylcyclohexyl | 2-methyl-5-butyl-N-pyrrolyl | CH | CH | CH | CH | R |
| 127 | ethyl | N-morpholinyl | (R,R,R,)-5-ethoxy-2-methylcyclohexyl | 2,5-dimethyl-N-pyrrolyl | CH | CH | CH | CH | R |
| 128 | ethyl | N-morpholinyl | (1R, 2R)-2-methylcyclohexyl | Z-3-(2-methyl)-3-heptenyl | CH | N | CH | CH | R |
| 129 | ethyl | N-morpholinyl | (R,R,R)-5-(1-methyl-1- | Z-3-(2-methyl)-3-heptenyl | CH | N | CH | CH | R |

-continued

| # | B | D | G | J | W | X | Y | Z | R/S |
|---|---|---|---|---|---|---|---|---|-----|
| 130 | ethyl | N-morpholinyl | (R,R,R)-5-(1-methoxyethyl)-2-methylcyclohexyl ethoxy-2-methylcyclohexyl | Z-3-(2-methyl)-3-heptenyl | CH | N | CH | CH | R |
| 131 | E-(1-methyl) ethenyl | 4-pyranyl | (1R, 2R)-2-methylcyclohexyl | Z-3-(1-methoxy)-2-hexenyl | CH | N | CH | CH | R/S |
| 132 | ethyl | N-morpholinyl | (2S, 4R)-4-ethoxy-N-aceto-2-pyrrolidinyl | Z-3-(2-methyl)-3-heptenyl | CH | N | CH | CH | R |
| 133 | ethyl | N-morpholinyl | (R,R,R)-5-(1-methyl-1-methoxyethyl)-2-methylcyclohexyl | Z-2-(2-hexenyl) | CH | N | CH | CH | R |

The compounds of this invention may be obtained using any conventional technique. Preferably, these compounds are chemically synthesized from readily available starting materials, such as alpha-amino acids. Modular and convergent methods for the synthesis of these compounds are also preferred. In a convergent approach, for example, large sections of the final product are brought together in the last stages of the synthesis, rather than by incremental addition of small pieces to a growing molecular chain. Various synthesis schemes for these compounds are presented in the examples of this application.

The compounds utilized in the compositions and methods of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of this invention are characterized by the ability to increase, restore or maintain the sensitivity of MDR cells to cytotoxic compounds, such as, for example, those typically used in chemotherapy. Based on that ability, the compounds of this invention are advantageously used to increase the effectiveness of chemotherapy in individuals who are afflicted with drug-resistant cancers, tumors, metastases or disease. In addition, the compounds of this invention are capable of maintaining sensitivity to therapeutic or prophylactic agents in non-resistant cells. Therefore, the compounds of this invention are useful in treating or preventing multi-drug resistance ("MDR") in a patient. More specifically, these compounds are useful in treating or preventing P-glycoprotein-mediated MDR and MRP-mediated MDR.

The compounds of this invention are also characterized by their ability to stimulate neurite growth through their binding affinity for FKBP-12. Based on that ability, the compounds of this invention may be used to stimulate nerve growth in a patient who has suffered nerve damage as a result of trauma or disease.

As used throughout this application, the term "patient" refers to mammals, including humans.

Multi-drug resistance has been explained in the art thus far by the presence of two independent proteins within the cell—the MDR1 P-glycoprotein or the MRP protein. Methods for quantitating the effectiveness of the compounds of this invention towards restoring drug sensitivity caused by either protein are known. For example, any assay known to measure the restoration of the anti-proliferative activity of a drug may be employed to test the compounds of this invention. These assays utilize cell lines resistant to particular drugs, and characterized by the presence of one or both of MDR1 and MRP. These cell lines include HL60/ADR, L1210, P338D, CHO and MCF7. The cell line is then exposed to compounds of this invention in the presence or absence of the drug to which it is resistant, such as doxorubicin.

The neutrotrophic activity of the compounds of this invention is directly related to their affinity for FKBP12 and their ability to inhibit FKBP12 rotomase activity. In order to candidate these properties, several assays known in the art may be employed. For example, competitive LH20 binding assays using labelled FK-506 as a reporting ligand have been described by M. W. Harding et al., Nature, 341, pp. 758–60 (1989) and by J. J. Siekiera et al., Nature, 341, pp. 755–57 (1989).

Preferably, the assay measures inhibition of FKBP12 rotomase activity. Such an assay has also been described by M. W. Harding et al., supra and by J. J. Siekierka et al., supra. In this assay the isomerization of an artificial substrate—N-succinyl-Ala-Ala-Pro-Phe-p-nitroanilide—is followed spectrophotometrically. The assay includes the cis form of the substrate, FKBP12, the inhibitor and chymotrypsin. Chymotrypsin is able to cleave p-nitroanilide from the trans form of the substrate, but not the cis form. Release of p-nitroanilide is measured.

According to another embodiment, the invention provides pharmaceutical compositions comprising the compounds of this invention or pharmaceutically acceptable derivatives thereof in an amount effective for the treatment or prevention of multi-drug resistance. According to another embodiment, the invention provides pharmaceutical compositions comprising the compounds of this invention or pharmaceutically acceptable derivatives thereof in an amount effective for stimulating neurite growth. A "pharmaceutically acceptable derivative" denotes any pharmaceutically acceptable salt, ester, or salt of such ester, of a compound of this invention or any other compound which, upon administration to a patient, is capable of providing or indirectly a compound of this invention.

Pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The pharmaceutical compositions of this invention further comprise a pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, polyethylene glycol and wool fat.

According to this invention, the pharmaceutical compositions may be in the form of a sterile parenteral preparation, for example a sterile injectable aqueous or oleaginous suspension. The term "parenteral" as used herein includes subcutaneous, intravenous, intramuscular, intra-articular, intra-synovial, intrasternal, intrathecal, intrahepatic, intralesional and intracranial injection or infusion techniques.

This parenteral preparation may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the jug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex and diet of the patient, the time of administration and rate of excretion of the compound, the particular drug combination, and the judgment of the treating physician and the severity of the particular disease being treated. The amount of active ingredient may also depend upon the therapeutic or prophylactic agent, it any, with which the ingredient is co-administered.

According to a preferred embodiment, the compounds of this invention are administered in combination with a therapeutic agent or a neurotrophic agent, depending upon the desired use.

For example, in order to increase the susceptibility of the MDR cells within the patient, the compounds of this invention may be administered with one or more chemotherapeutic agents, such as actinomycin D, doxorubicin, vincristine, vinblastine, etoposide, amsacrine, mitoxantrone, tenipaside, taxol or colchicine. For the same purpose, the compounds of this invention may also be used in combination with a chemosensitizing agent, such as cyclosporin A and its analogs, phenothiazines or thioxantheres. As used in this application, the term "chemosensitizing agent", excludes the compounds of this invention.

For neurotrophic use, the compounds of this invention may be combined with other neurotrophic factors, such as nerve growth factor (NGF), insulin growth factor (IGF-1)

and its active truncated derivatives such as gIGF-1, acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3)and neurotrophin 4/5 (NT-4/5). As used in this application, the term "neurotrophic factor" excludes the FKBP12 binding compounds described herein, as well as FK-506 and rapamycin.

The additional agent may be part of a single pharmaceutical composition or may be separately administered sequentially or concurrently to the patient. Thus, according to one preferred embodiment, the pharmaceutical compositions of this invention comprise a compound of this invention and a chemosensitizing agent. According to another preferred embodiment, the pharmaceutical compositions of this invention comprise a compound of this invention and a chemotherapeutic agent. According to yet another preferred embodiment, the pharmaceutical compositions of this invention comprise a compound of this invention and a neurotrophic agent.

According to another embodiment, the invention provides methods for treating or preventing multi-drug resistance in a patient by administering a composition of this invention. Effective dosage levels for treating or preventing MDR range from between about 0.01 and about 100 mg/kg body weight per day, preferably between about 0.5 and about 50 mg/kg body weight per day of a compound of this invention. A typical composition for use in treating MDR will contain between about 5% and about 95% of active compound(s) (w/w), whether it be solely one of the compounds of this invention or a combination of a compound of this invention and another chemotherapeutic or chemosensitizing agent. Preferably, such preparations contain between about 20% and about 80% active compound(s).

The amount of chemosensitizing or chemotherapeutic agent used in combination with the compounds of this invention, whether part of the same composition or separately administered, will be less than that used in a monotherapy. Preferably, the amount of chemosensitizing or chemotherapeutic agent is less than 80% of the dosage used in a monotherapy. Monotherapeutic dosages of such agents are known in the art.

In another embodiment, the invention provides methods for stimulating neurite outgrowth by administering a composition of this invention. The amount of the compound and, optionally, a neurotrophic factor that may be combined with the carrier materials to produce a single dosage form will vary depending upon the host treated, the particular mode of administration. The two active ingredients of the pharmaceutical compositions of this invention act synergistically to stimulate neurite outgrowth.

In the treatment of multi-drug resistance or stimulation of neurite outgrowth, dosage levels of between about 0.01 and about 100 mg/kg body weight per day, preferably between about 0.5 and about 50 mg/kg body weight per day of the active ingredient compound are useful. A typical preparation will contain between about 5% and about 95% active compound (w/w). Preferably, such preparations contain between about 20% and about 80% active compound.

The amount of the neurotrophic factor in these compositions and combination therapies will be less than that required in a monotherapy utilizing only that neurotrophic factor. Preferably, the compositions should be formulated so that a dosage of between 0.01–100 mg/kg body weight/day of the compounds of this invention can be administered. The neurotrophic factor, whether part of the same composition or separately administered, should be given at a dosage of between 0.01–100 μg/kg body weight/day.

The neurotrophic methods and compositions of this invention may be used to treat nerve damage caused by a wide variety of diseases or physical traumas. These include, but are not limited to, Alzheimer's disease, Parkinson's disease, ALS, stroke and ischemia associated with stroke, neural paropathy, other neural degenerative diseases, motor neuron diseases, sciatic crush, spinal cord injuries and facial nerve crush.

In order that this invention may be more fully understood, the following examples are set forth. These examples are for the purpose of illustration only and are not to be construed as limiting the scope of the invention in any way.

EXAMPLE 1

Preparation of Compound 11

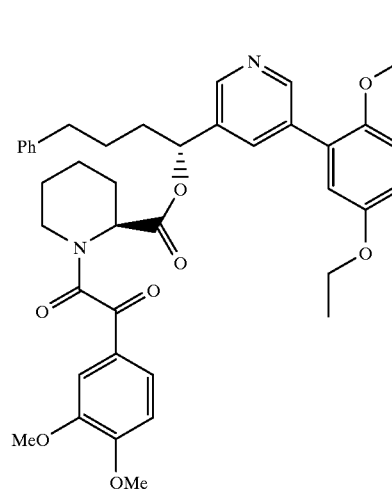

11

To a solution of bromohydroquinone (10.0 g, 0.053 mol) in DMF (70 mL) was added 1-bromopropane (39.0 g, 0.318 mol) and cesium carbonate (50 g, 0.153 mol) and heated at 90° C. for 2 days. The reaction mixture was filtered through Celite and washed with ethyl acetate (500 mL). The solution was concentrated and chromatographed on silica gel eluting with 0.25% ethyl acetate-hexane to yield 9.0 g (62%) of the bromobenzene (136) as a colorless oil; $^1$H NMR (500 MHz, CDCl$_3$) (136) δ 7.08(d,1H), 6.80 (dd,1H), 6.77(dd,1H), 4.00(q,2H), 3.93(q,2H), 1.40(t,3H), 1.38(t,3H).

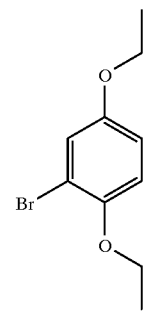

To a solution of the bromobenzene (136) (6.6 g, 24.2 mmole) in THF (50 mL) was added dropwise n-BuLi in hexane (1.6M, 33 ml, 52.9 mmole) at −78° C. under a N$_2$ atmosphere, and stirred at the same temperature for 1 hr. The resulting mixture was treated with trimethylborate (9.0 ml, 79.5 mmole) at −78° C. and allowed to warm to room temperature over 3 hrs. Aqueous HCl (100 mL, 7%) was added to the reaction mixture and stirred overnight at room temperature. The aqueous layer was washed with CH₂Cl₂. All the organics were combined and dried over MgSO₄. The solution was concentrated and chromatographed on silica gel eluting with 0.5% methanol-CH₂Cl₂ to 2% methanol—CH₂Cl₂ to yield the boronic acid (137) (4.3 g, 75%) as a colorless solid; $^1$H NMR (500 MHz, CDCl₃) (137( δ 7.38 (d,1H), 6.94(dd,1H), 6.81(d,1H), 6.46(brs,2H), 4.08(q,2H), 4.02(q,2H).

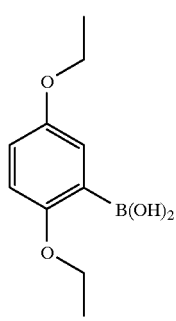

137

To a solution of 5-bromonicotinic acid (5.0 g, 24.8 mmole) in a mixture of CH₂Cl₂ (50 mL) and DMF(5 mL) was added 1-(3-dimethylaminopropyl)-3-ethylcarbodiimide hydrochloride (5.21 g, 27.2 mmole), N,O-dimethylhydroxylamine hydrochloride (2.66 g, 27.2 mmole) and diisopropylethyl-amine (4.74 ml, 27.2 mmole), and the mixture stirred at room temperature overnight. The reaction mixture was diluted with CH₂Cl₂ (200 mL) and washed with water (100 ml×3). The organic phase was dried over MgSO₄ and concentrated. The crude oil was chromatographed on silica gel eluting with 33% ethyl acetate-hexanes to yield the bromopyridine (138)(4.5 g, 74%) as a colorless oil; $^1$H NMR (500MHz, CDCl₃) (138) d 8.73(dd,1H), 8.62(dd,₁H), 8.08 (dd,1H), 3.47(s,3H), 3.27(s,3H).

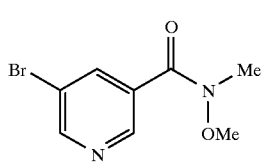

138

To a solution of the amide (138) (4.2 g, 17.1 mmole) in THF (40 mL) was added dropwise phenylpropylmagnesium bromide (0.5 M, 70 ml, 35.0 mmole) prepared from 1-bromo-3-phenylpropane and magnesium at 0° C. for 2 hrs. The reaction mixture was quenched with aqueous NH₄Cl (5 mL), and extracted with ethyl acetate (300 mL). The organics were dried over MgSO₄, concentrated and chromatographed on silica gel eluting with 20% ethyl acetate-hexanes to yield the ketone (139)(2.34 g, 45%) as a colorless oil; $^1$H NMR (500 MHz, CDCl₃) (139) δ 8.98(dd,1H), 8.80(dd,1H), 8.30(dd,1H), 7.40–7.12(m,5H), 2.92(t,2H), 2.70(t,2H), 2.10 (tt,2H).

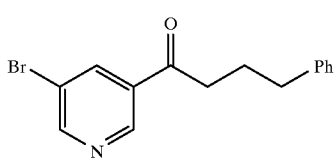

139

To a stirred mixture of the bromopyridine (139) (304 mg, 1.0 mmole) and tetrakis(triphenylphosphine)-palladium(0) (30 mg, 0.024 mmole) in toluene (30 mL) was successively added the boronic acid (137)(420 mg, 2 mmole) dissolved in 2 ml of ethanol and sodium carbonate (420 mg, 4 mmole) dissolved in 2 ml of H₂O. The resulting solution was heated at reflux for 2 hrs, and allowed to cool to room temperature. The solution was diluted with ethyl acetate (100 mL), and the separated organic phase was dried over MgSO₄. The solution was concentrated and chromatographed on silica gel eluting with 20% ethyl acetate-hexanes to yield the biaryl (140)(215 mg, 55%) as a colorless oil; $^1$H NMR (500 MHz,CDCl₃) (140) δ9.04 (d,1H), 8.93(d,1H), 8.39(dd,1H), 7.30–7.22(m,2H), 7.21–7.14(m,3H), 6.97–6.85(m,3H), 4.02 (q,2H), 3.96(q,2H), 2.99(t,2H), 2.74(t,2H), 2.12(tt,2H), 1.40 (t,3H), 1.28(t,3H).

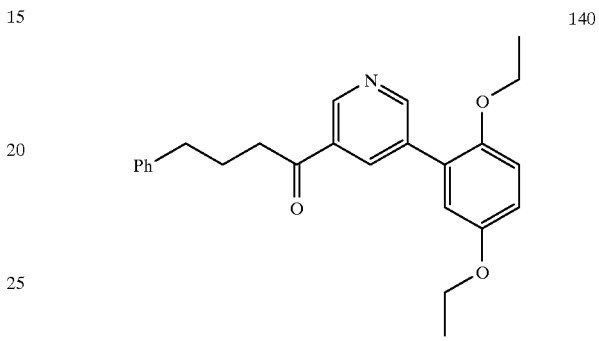

140

To a solution of the ketone (140) (210 mg, 0.54 mmole) in methanol (10 mL) at 0° C. was added sodium borohydride (30 mg, 0.79 mmole), and the mixture stirred at room temperature for 20 min. The reaction mixture was quenched with water (1 mL) and concentrated. The residual oil was extracted with CH₂Cl₂ and the organic phase was dried over MgSO₄. The solution was concentrated and chromatographed on silica gel eluting with 50% ethyl acetate-hexanes to yield the alcohol (141) (157 mg, 74%) as a colorless oil; $^1$H NMR (500 MHz, CDCl₃) (141) δ 8.60(d,1H), 8.39(d, 1H), 7.90(dd,1H), 7.27–7.19(m,2H), 6.90–6.80(m,5H), 4.75–4.68(m,1H), 3.98(q,2H), 3.90(q,2H), 3.20(brs,1H), 2.67–2.57(m,2H), 1.91–1.58(m,4H), 1.39(t,3H), 1.24(t,3H).

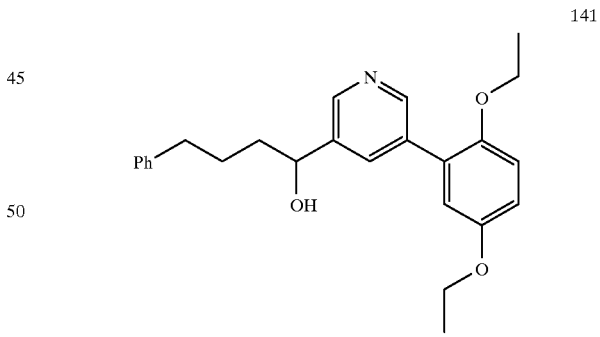

141

To a solution of the alcohol (141) in CH₂Cl₂ (10 mL) was added (S)—N—2-trimethylsilylethoxycarbonyl-pipecolinic acid (210 mg, 0.77 mmole), N-ethyl-N'—1-(3-dimethylaminopropyl)-carbodiimide hydrochloride (150 mg, 0.77 mmole), and dimethylaminopyridine (3 mg, 0.025 mmole). The resulting mixture was stirred at room temperature for 14 hrs, and quenched by adding H₂O (5 mL). The mixture was diluted with CH₂Cl₂ (20 mL). The organic phase was dried over MgSO₄. The solution was concentrated and chromatographed on silica gel eluting with 20% ethyl acetate-hexane to yield the ester (142) (230 mg, 93%) as a colorless oil; ¹H NMR (500 MHz, CDCl₃) (142) δ 8.70(d, 1H), 8.48(d,1H), 7.80(dd,1H), 7.28–7.18(m,2H), 7.17–7.07 (m,3H), 6.93–6.82(m,5H), 5.90–5.80(m,1H), 4.98–4.92 and 4.82–4.72(m,1H), 4.22–3.84(m,6H), 3.02–2.83(m,1H), 2.60 (t,2H), 2.28–2.12(m,1H), 2.07–1.91(m,1H), 1.90–1.80(m, 1H), 1.78–0.78(m,16H), 0.05–0.15(m,9H).

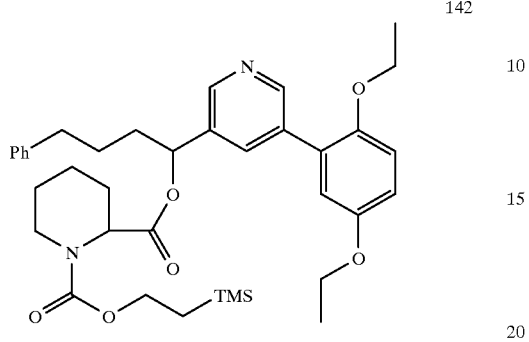

142

To a solution of the ester (142) (220 mg, 0.34 mmole) in acetonitrile (15 mL) was added cesium fluoride (800 mg, 5.26 mmole) and the suspension heated at reflux for 14 hrs. The reaction mixture was allowed to cool to room temperature and diluted with CH₂Cl₂ (100 mL). The mixture was vacuum filtered through Celite and washed with CH₂Cl₂. The solution was concentrated and chromatographed on silica gel eluting with 2% MeOH—CH₂Cl₂ to 5% MeOH—CH₂Cl₂ to yield the amine (143) (85 mg, 50%) as a colorless oil; ¹H NMR (500 MHz,CDCl₃) (143) δ 8.70(d,1H), 8.48 (d,1H), 7.82(dd,1H), 7.28–7.20(m,2H), 7.19–7.08(m,3H), 6.92–6.81(m,3H), 5.88–5.82(m,1H), 4.06–3.98(m,2H), 3.97–3.89(m,2H), 3.41–3.31(m,1H), 3.08–3.01(m,1H), 2.69–2.55(m,2H), 2.10–1.32(m,15H), 1.30–1.21(m,3H).

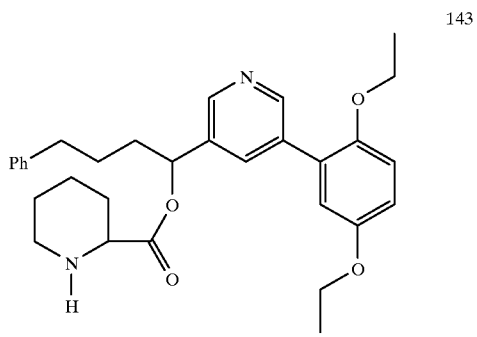

143

To a solution of the amine (143) (40 mg, 0.080 mmole) in CH₂Cl₂ (5 mL) was added 3,4-dimethoxybenzoylformic acid (85 mg, 0.405 mmole) and N-ethyl-N'—1-(3-dimethylaminopropyl)-carbodiimide hydrochloride (80 mg, 0.417 mmole). The resulting mixture was stirred at room temperature for 5 days, and quenched by adding H₂O (5 mL). The mixture was diluted with CH₂Cl₂ (20 mL), the layers separated and the organic phase was dried over MgSO₄. The solution was concentrated and chromatographed on silica gel eluting with 0.5% MeOH—CH₂Cl₂ to 1.0% MeOH—CH₂Cl₂ to yield 11 (6.8 mg, 24%) and the diastereomer of compound 11 (8.9 mg, 32%) as a colorless oils; TLC Rf=0.20 (2.5% CH₂Cl₂/MeOH) (Compound 11), Rf=0.23 (2.5% CH₂Cl₂/MeOH) (The diastereomer of compound 11); ¹H NMR (500 MHz, CDCl₃) (11) δ 8.72 and 8.68(d,1H) 8.53 and 8.36(d,1H), 7.87 and 7.74(m,1H), 7.63–7.06(m,8H), 6.87(m,3H), 5.95 and 5.80(dd,1H), 6.40 (m,1H), 4.07–3.82(m,10H), 3.48(m,1H), 3.18 and 2.96(dt, 1H), 2.65 and 2.58(t,2H), 2.40 and 2.20(m,1H), 2.15–1.19 (m,15H).

EXAMPLE 2

Preparation of Compound 79

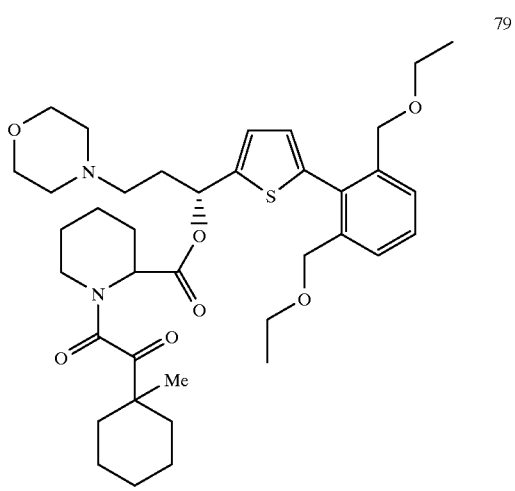

79

To a boiling mixture of 300 g (2.32 mole) of D,L-pipecolinic acid in methanol (1.23 L) was added 348 g (2.32 mole) of D-Tartaric acid. The solution was allowed to stir for five minutes and then cooled to room temperature. The salt was filtered and washed with methanol and was purified by recrystallization two times from water/acetone to give 124.2 g of 144.

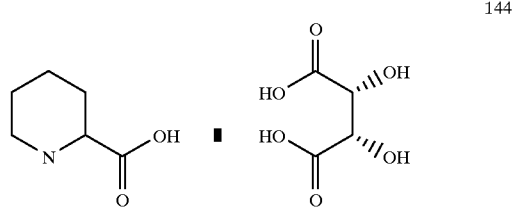

144

To a stirred mixture of 124.2 g (0.445 mole) of 144 and 340 ml (1.95 mole) of N,N-diisopropylethylamine at 0° C. was added 282 ml (2.23 mole) of chlorotrimethyl-silane dropwise. The mixture was allowed to warm to room temperature and stir for one hour. The mixture was re-cooled to 0° C. and treated with 85 ml (0.49 mole) of N,N-diisopropylethylamine followed by the dropwise addition of 102 g (0.467 mole) of di-t-butyldicarbonate dissolved in methylene chloride (270 ml). The reaction was allowed to warm to room temperature and stir overnight. The solvent was evaporated under reduced pressure, basified with 1 N aqueous NaOH, and washed with ether. The aqueous phase was acidified with aqueous KHSO₄, extracted with ether, and the organic phase dried over MgSO₄. The solvent was evaporated under reduced pressure and purified by recrystallization from ethyl acetate/hexanes to give 76 g of optically pure 145.

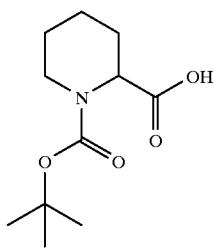

145

A solution of 3.6 g (15.7 mmole) of 145 in ethanol (30 ml) was cooled to 0° C., subjected to a stream of HCl(g) for fifteen minutes, and allowed to stir for 48 hr at room temperature. The solvent was evaporated under reduced pressure and the resulting residue dissolved in methylene chloride. This solution was washed two times with NaHCO$_3$ (aq) and once with brine, dried over Na$_2$SO$_4$ and the solvent was evaporated under reduced pressure to give 2.5 g of 146.

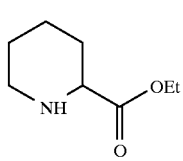

146

To a stirred solution of 2.5 g (14.0 mmole) of 146 and 3.4 ml (19.1 mmole) of N,N-diisopropylethylamine at 0° C. was added 1.6 ml (17.5 mmole) of methyloxalyl chloride. The mixture was allowed to stir for thirty-five minutes, diluted with methylene chloride, washed once with water, once with brine, and dried over Na$_2$SO$_4$. The solvent was evaporated under reduced pressure and purified by chromatography on silicate gel using 9:1 hexane:ethyl acetate as eluent to give 3.52 g of 147.

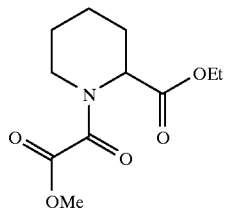

147

LiBr (12.3 g, 142 mmole) was dissolved into 1-Methylcyclohexanol (10.8 g, 94.6 mmole) with gentle heating. To this was added 5 mL of 48%HBr, the mixture was cooled to 0° C. and a further 17 mL HBr(aq) added in a dropwise fashion. This was stirred for 3.5 h at which point the upper layer was separated, washed with ethylene glycol, diluted with ether and then dried over Na$_2$SO$_4$. The filtered solution was carefully concentrated to yield 12.4 g (70 mmole, 74%) of 1-bromo-1-methylcyclohexane (148) as a light yellow oil, greater than 95% pure by tlc and $^1$H NMR.

Bromide 148 (8.0 g, 45.2 mmole) was dissolved in 20 mL of THF and treated with 1.14 g (47.4 mmole) of Mg° turnings. The reaction was heated to 55° C., following initiation with 2 drops of 1,2-dibromoethane, for a total of 90 mins. Cooled to ambient temperature and used as Methyl-cyclohexyl Grignard (149).

The methyl oxamide (147, 1.5 g, 6.17 mmole), dissolved in 10 mL of CH$_2$Cl$_2$ at ambient temperature, was treated dropwise with portions of the grignard solution as prepared above. The reaction progress, as noted by conversion of starting material to the desired product, was monitored by tlc. Complete consumption or starting material required 5–6 eq's of the grignard reagent. The reaction was quenched by addition of 10% KHSO$_4$ and extracted with CH$_2$Cl$_2$. The organics were washed with water and brine, dried over MgSO$_4$ and concentrated. Elution from silica gel with 10% ethyl acetate in hexanes gave product (150) (712 mg, 37%) pure by tlc and $^1$H NMR.

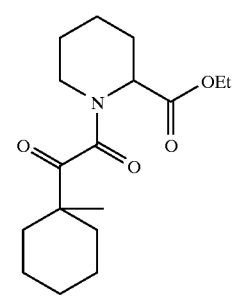

150

The ethyl ester 150 (575 mg, 1.86 mmole) was dissolved in 4 mL of THF at 0° C. and treated in a slow, dropwise fashion with 2 eq's of 1N LiOH. Brought to ambient temperature after 30 mins and allowed to stir overnight. The reaction was acidified with 10% KHSO$_4$, extracted with CH$_2$Cl$_2$, the organics washed with brine, dried over Na$_2$SO$_4$ and stripped to yield 510 mg (1.81 mmole, 98%) of acid 151, pure by $^1$HNMR and containing less than 0.5% of the epimer as determined by HPLC analysis.

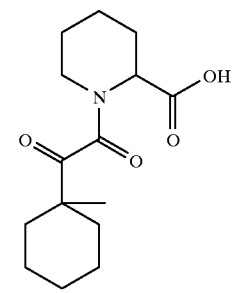

151

To a solution of 2-bromo-m-xylene (157 g, 0.849 mol) in carbon tetrachloride (1.5 L) was added N-bromosuccinimide (362 g, 2.034 mol) and benzoyl peroxide (1.38 g, 7.75 mmole), and heated at reflux for 3 hrs. The reaction mixture was allowed to cool to room temperature and washed with H$_2$O (500 ml×2), dried over MgSO$_4$ and concentrated. The obtained solid was washed with n-hexane(1 L) and recrystallized from i-PrOH to give the tribromide (152) as a colorless solid (98 g, 34%); $^1$H NMR (500 MHz, CDCl$_3$) (152) δ 7.40(d,2H), 7.26(dd,1H), 4.62(s,4H).

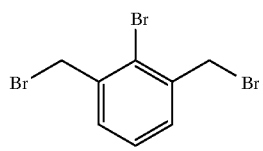

152

To a suspension of sodium hydride (18.6 g as an 80% dispersion in mineral oil, 0.62 mol) in anhydrous THF (80 mL) was added ethanol (34.1 mL, 0.583 mol) at 0° C. and stirred for 30 min. To the mixture was added tribromide (152) (33.0 g, 0.096 mol) and heated at 45° C. for 2 hrs. The reaction mixture was allowed to cool to room temperature and diluted with ethyl acetate (200 mL). The solution was washed with $H_2O$ and the organics dried over $MgSO_4$. The solution was concentrated and chromatographed on silica gel eluting with 30% $CH_2Cl_2$-hexanes to yield the diethyl-ester (153) (25.0 g, 95%) as a colorless oil; $^1H$ NMR (500 MHz, $CDCl_3$) (153) δ 7.40(d,2H), 7.30(dd,1H), 4.58(s,4H), 3.60(q,4H), 1.28(t,6H).

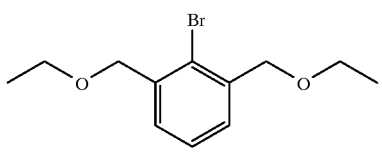

153

To a solution of the bromobenzene (153) (25.0 g, 91.6 mmole) in THF (250 mL, was added dropwise n-BuLi solution in hexane (1.6 M, 63 ml, 101 mmole) at −78° C. under N2 atmosphere, and stirred at the same temperature for 2 hr. To the resulting mixture was added trimethyl borate (34 ml, 0.3 mol) over 10 min at −78° C., and stirred for 2 hrs. The reaction mixture was allowed to warm to room temperature over 1 hr and stirred overnight. Aqueous 4 N HCl (300 mL) was added to the reaction mixture and stirred for 4 hrs. The mixture was concentrated to ca. 250 ml and extracted with $CH_2Cl_2$ (300 ml×3). The organics were extracted with 2N NaOH (200 ml×2). The combined aqueous layers were washed with $CH_2Cl_2$ and acidified to pH2 with 6N HCl. The mixture was extracted with $CH_2Cl_2$, dried over $MgSO_4$ and concentrated to yield the boronic acid (154) (10.5 g, 48%) as a colorless solid; $^1H$ NMR (500 MHZ,$CDCl_3$) (154) δ 7.58(s,2H), 7.33(dd,1H), 7.27(d,2H), 4.50(s,4H), 3.58(q,4H), 1.22(t,6H).

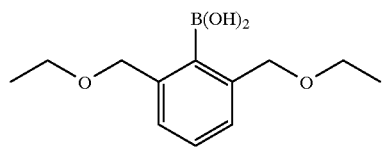

154

To a solution of 5-bromo-2-thiophenecarboxaldehyde (10.0 g, 52.4 mmole) in anhydrous THF (100 mL) was slowly added vinylmagnesium bromide (1.0M solution in THF, 60.0 ml, 60.0 mmole) at −78° C. and stirred for 1 hr. The reaction mixture was quenched by addition of sat. aqueous $NH_4Cl$ (10 mL), and allowed to concentrated. The obtained oil was chromatographed on silica gel eluting with 10% ethyl acetate-hexane to yield the alcohol (155) (6.0 g, 52%) as a colorless oil.

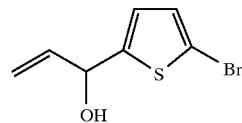

155

To a solution of the alcohol (152) (2.80 g, 12.6 mmole) in $CH_2Cl_2$ (100 mL) was added manganese (IV) oxide (5.0 g, 57.5 mmole) and morpholine (92.3 ml, 26.4 mmole) and the suspension was stirred at room temperature for 14 hrs. The mixture was vacuum filtered through Celite and washed with $CH_2Cl_2$. The solution was concentrated and chromatographed on silica gel eluting with 10% ethyl acetate-hexanes to yield the ketone (156) (3.5 g, 91%) as a colorless oil; $^1H$ NMR (500 MHz,$CDCl_3$) (156) δ 7.43(d,1H), 7.09(d,1H), 3.72–3.62(m,4H), 3.00(t,2H), 2.78(t,2H), 2.55–2.40(m,4H).

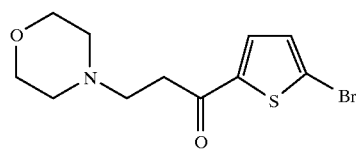

156

To a stirred mixture of the bromothiophene (156) (2.0 g, 6.6 mmole) and tetrakis(triphenylphosphine)-palladium(0) (500 mg, 0.402 mmole) in toluene (100 mL) was successively added the boronic acid (154)(2.57 g, 10.8 mmole) dissolved in 7 mL of ethanol and sodium carbonate monohydrate (2.74 g, 22.1 mmole) dissolved in 4 mL of $H_2O$. The resulting solution mixture was heated at reflux for 14 hrs, and allowed to cool to room temperature. The solution was diluted with ethyl acetate (200 mL), and the separated organic phase was dried over $MgSO_4$. The solution was concentrated and chromatographed on silica gel eluting with 10% ethyl acetate-hexanes to yield the biaryl (157) (2.16 g, 79%) as a colorless oil; $^1H$ NMR (500 MHz,$CDCl_3$) (157) δ 7.68 (d,1H), 7.44(d,2H), 7.42–7.38(m,1H), 6.94(d,1H), 4.24(s,4H), 3.68(t,4H), 3.37(q,4H), 3.10(t,2H), 2.83(t,2H), 2.49(t,4H), 1.12(t,6H).

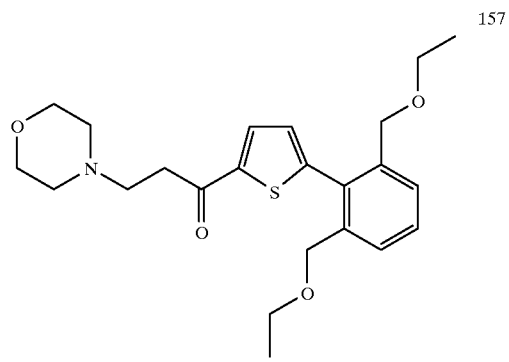

157

To a suspension of lithium alminum hydride (170 mg, 4.48 mmole) in anhydrous THF (20 mL) was added dropwise a solution of the ketone (157) (1.82 g, 4.36 mmole) in anhydrous THF (10 mL) at −40° C., and the mixture stirred for 20 min. The reaction mixture was quenched by addition of Rochelle salt aqueous solution (5 mL), and stirred overnight at room temperature. The solution was extracted with ethyl acetate (50 mL×2), and the extracts were dried over MgSO₄, concentrated and chromatographed on silica gel eluting with 2.5% MeOH—CH₂Cl₂ to yield the alcohol (158) (1.54 g, 84% as a colorless oil; ¹H NMR (500 MHz,CDCl₃) (158) δ 7.44(d,2H), 7.38(d,1H), 6.88(d,1H), 6.72(d,1H), 5.16(t,1H), 4.29(s,4H), 3.70(t,4H), 3.38(q,4H), 2.68(t,2H), 2.47(brs,1H), 1.98(dt,2H), 1.16(t,6H).

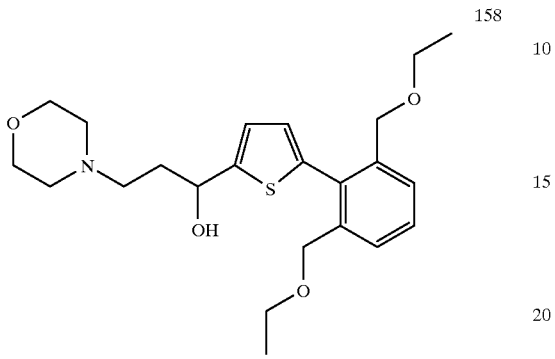

To a solution of the alcohol (158) in CH₂Cl₂ (10 mL) was added (R)-(−)-α-methoxyphenylacetic acid (1.22 g, 7.36 mmole), N-ethyl-N'—1-(3-dimethylaminopropyl)-carbodiimide hydrochloride (1.41 g, 7.36 mmole), and 4-dimethylaminopyridine (3 mg, 0.025 mmole). The resulting mixture was stirred at room temperature for 2 hrs, and quenched by adding H₂O(5 mL). The mixture was diluted with CH₂Cl₂ (20 mL). The organic phase was dried over MgSO₄, and the solution concentrated and chromatographed on silica gel eluting with diethyl ether to provide the diastereomeric mixture (1.51 g, 72%) of the esters as colorless oils. The ester (159) was isolated (290 mg, 28%) in pure form through further silica gel chromatography, eluting with diethyl ether; TLC Rf=0.24 (diethyl ether) (Compound 159), Rf=0.31 (diethyl ether) (The diastereomer of compound 159); ¹H NMR 500 MHz, CDCl₃) (159) δ 7.46–7.18 (m,8H), 6.83(t,1H), 6.62(d,1H), 6.18(t,1H), 4.77(s,1H), 4.17 (s,4H), 3.65(m,4H), 3.40–3.23(m,7H), 2.40–1.98(m,8H), 1.13(t,6H.

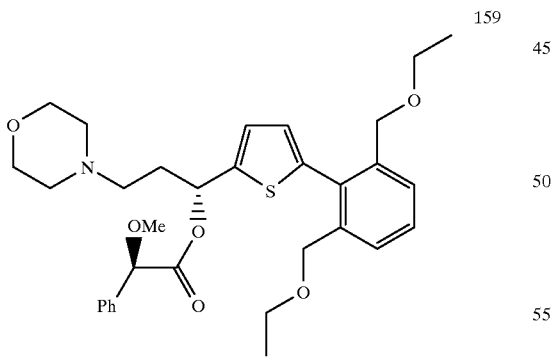

To a solution of the ester (159) (290 mg, 0.511 mmole) in methanol (1 mL) was added 1N NaOH solution (4 mL, 4 mmole) at room temperature and the mixture stirred for 1 hr. The solution was concentrated and extracted with CH₂Cl₂ (10 ml×2). The extracts were dried over MgSO₄, concentrated and chromatographed on silica gel eluting with 5% of MeOH—CH₂Cl₂ to yield the alcohol (160)(210 mg, 98%) as a colorless oil; ¹H NMR (500 MHz, CDCl₃) (160) δ 7.44 (d,2H), 7.38(d,1H), 6.88(d,1H), 6.72(d,1H), 5.16(t,1H), 4.29 (s,4H), 3.70(t,4H), 3.38(q,4H), 2.68(t,2H), 2.50(brs,1H), 1.98(dt,2H), 1.16(t,6H).

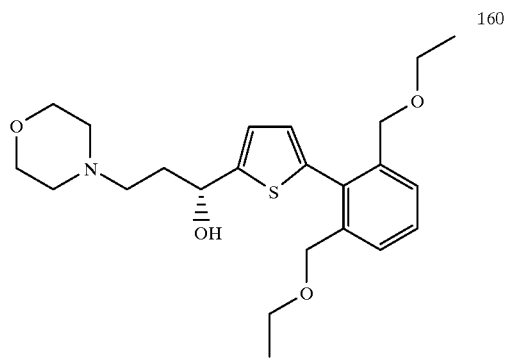

To a solution of the alcohol (160) (20 mg, 0.048 mmole) in CH₂Cl₂ (2 mL) was added the acid (151) (35 mg, 0.124 mmole) and 1,3-d-cyclohexylcarbodiimide (25 mg, 0.121 mmole), (−)-camphorsulfonic acid (8.0 mg, 0.0345 mmole) and 4-dimethylaminopyridine (4.0 mg, 0.0328 mmole). The resulting mixture was stirred at room temperature for 6 days, and quenched by adding H₂O (1 mL) The aqueous layer was extracted with CH₂Cl₂ (5 ml×2). The combined organics were dried over MgSO₄ and concentrated. The obtained oil was chromatographed on silica gel eluting with 1% MeOH—CH₂Cl₂ to 2% MeOH—CH₂Cl₂. The fractions containing the ester (79) were collected and concentrated and the resulting oil was chromatographed on silica gel eluting with 30% ethyl acetate-hexanes to 50% of ethyl acetate-hexanes to yield the ester (79) (11 mg, 34%) as a colorless solid; TLC Rf=0.30 (5% CH₂Cl₂/MeOH); ¹H NMR(500 MHz, CDCl₃) δ 7.50 (d,2H), 7.40(dd,1H), 7.07 (d,1H), 6.75(d,,1H), 6.22(dd,1H), 5.20(m,1H), 4.25(s,4H), 3.72(m,4H), 3.38(m,4H), 3.10 and 2.88 (dt,1H), 2.50–1.20 (m,25H), 1.28 (s,3H), 1.15(t,6H).

EXAMPLE 3

Preparation of Compound 78

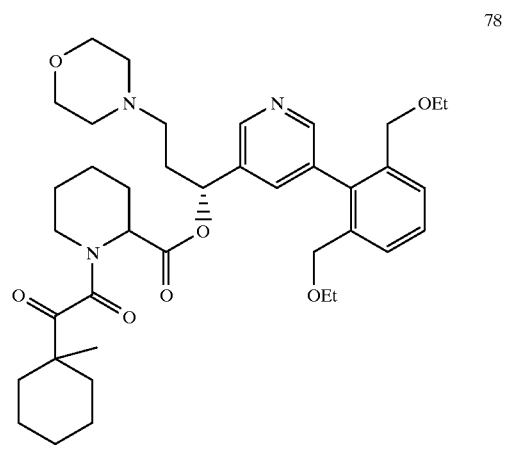

To a solution of 138 (6.17 g, 25.2 mmol) and tetrakis (triphenylphosphine)-palladium(0) (0.55 g, 0.48 mmol) in toluene (300 mL) was added 154 (5.00 g, 21.0 mmol) in ethanol (20 mL) and sodium carbonate monohydrate (5.20 g, 42 mmol) in water 20 mL). The solution was heated at reflux for 16 hours and the layers separated. The aqueous layer was extracted with ethyl acetate, and the combined organics dried (MgSO$_4$) and concentrated to an oil. Purification by flash chromatography (1:1 ethyl acetate:hexane as eluent) yielded 6.00 g (80%) of 152 as a colorless oil.

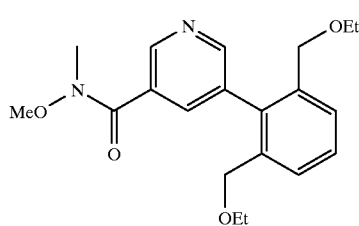

152

To a solution of 152$^1$ (485 mg, 1.35 mmol) in THF (5 mL) at 0° C. was added vinyl grignard (6.8 ml of 1.0 M solution in THF, 6.8 mmol) and the reaction stirred at 0° C. for 1 hour. Morpholine (235 mg, 2.70 mmol) was added, and the reaction quenched with water. The reaction mixture was extracted with ethyl ether and the combined organics dried (MgSO$_4$) and concentrated to an oil. Purification by flash chromatography, eluting with 0 to 5% ethanol in ethyl ether, yielded 245 mg (45%) of 161 as a pale yellow oil.

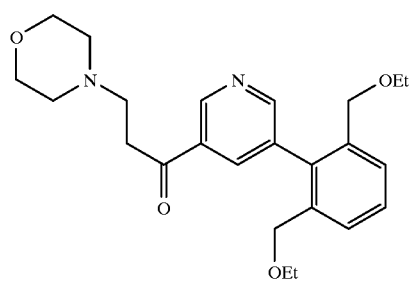

161

To a solution of 161 (240 mg, 0.58 mmol) in THF at −40° C. was added lithium aluminum hydride (23 mg, 0.61 mmol). The reaction was stirred for 20 minutes, quenched with Rochelle's salt and extracted with ethyl acetate. Combined organics were dried (MgSO$_4$) and concentrated to an oil. Purification by flash chromatography (2 to 3% methanol in methylene chloride as eluent) yielded

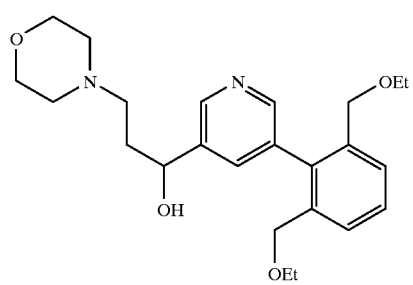

162 compound 162 (170 mg, 71%) as a colorless oil.

A solution of 162 (170 mg, 0.41 mmol), S-(+)-α-methoxyphenylacetic acid (206 mg, 1.24 mmol), 1-(3-dimethylaminopropyl)-3-ethylcarbodiimide (238 mg, 1.24 mmol) and catalytic DMAP were combined in dry methylene chloride (5 mL) and stirred for 3 days. The reaction mixture was diluted with methylene chloride and washed with water and saturated bicarbonate solution. The methylene chloride layer was dried (MgSO$_4$) and concentrated to a yellow oil. Purification by flash chromatography (2% ethanol in ethyl ether as eluent) yielded 45 mg (20%) of the less polar diastereomer 163 and 29 mg (13%) of the more polar diastereomer 164 as colorless oils.

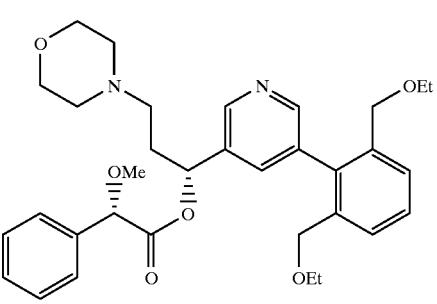

163

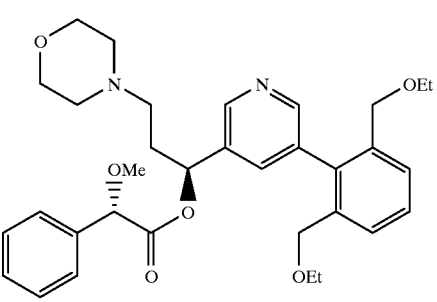

164

To a solution of 163 (42 mg, 0.075 mmol) in methanol (2 mL) at 0° C. was added 1N NaOH (112 uL, 0.112 mmol) and the reaction mixture stirred for 1.5 hours. The mixture was diluted with water and extracted with methylene chloride. Combined organics were dried (MgSO$_4$) and concentrated to yield 165(30 mg, 97%) as a colorless oil.

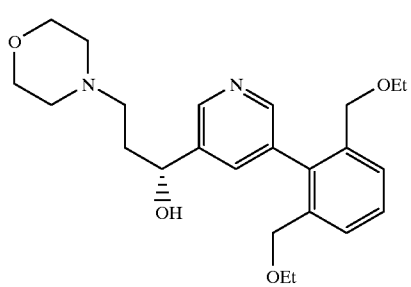

165

Compound 165 (23 mg, 0.055 mmol), 151(24 mg, 0.0825 mmol), 1,3-dicyclohexylcarbodiimide (19 mg, 0.0935 mmol) and catalytic camphorsulfonic acid and DMAP were combined in dry methylene chloride (1 mL) and the solution stirred overnight. The methylene chloride was removed in vacuo and the resulting oil purified by chromatography, eluting with 1 to 5% ethanol in methylene chloride, to yield 78 (24 mg, 65%) as a colorless oil and mixture of rotomers. $^1$H—NMR (500 MHz, CDCl3): 1.10 (dt, 6H), 1.24 and 1.15 (s, 1H) 1.36 (m, 8H), 1.93 (m, 4H), 2.3 (m, 8H), 3.13 and 2.88 (dt, 1H), 3.29 (m, 4H), 3.39 and 4.43 (br d, 1H), 3.67 dd, 4H) 4.08(dd,4H) 5.25 and 4.20 (br d, 1H), 5.98 (t, 1H), 7.42 (m, 3H) 7.59 (s, 1H) 8.46 (d, 1H) 8.67 and 8.62 (d, 1H)

EXAMPLE 4

Preparation of Compound 82

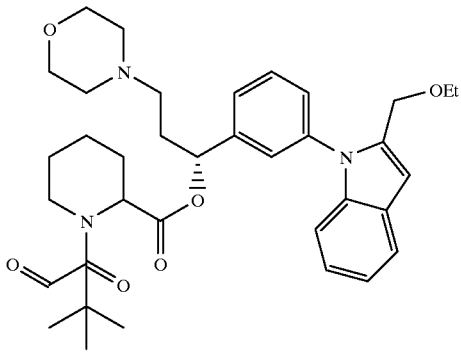

82

To a stirred solution of 21.45 g (113 mmole) of ethylindole-3-carboxylate and 66 ml (567 mmole) of 3-bromobenzaldehyde in DMF (35 ml) was added 81 g (567 mmole) of copper(I)oxide and the suspension heated at 120° C. overnight. The reaction mixture was filtered through celite and partitioned with water and ethyl acetate. The organic phase was washed two times with aqueous potassium bisulfate, two times with aqueous sodium bicarbonate, two times with water, once with brine and dried over magnesium sulfate. The solvent was evaporated under reduced pressure and the residue was purified by chromatography on silica gel, using 3:1 methylene chloride/hexane as eluent to give 4.21 g of 166.

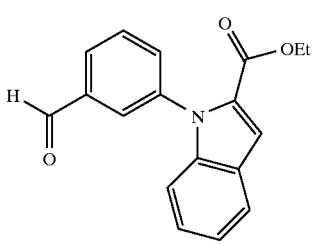

166

To a stirred solution of 3.0 g (10.2 mmole) of 166 at −78° C. in THF (30 ml) was added 25.6 ml (25.6 mmole) of 1M vinylmagnesium bromide in THF dropwise. The mixture was allowed to warm to −30° C. and stir for ½ hour. Reaction was quenched with aqueous ammonium chloride and extracted with ethyl acetate. The organic phase was washed once with brine and dried over magnesium sulfate. The solvent was evaporated under reduced pressure and the residue was purified by chromatography on silica gel, using 7:3 hexane/diethyl ether to give 1.80 g of 167.

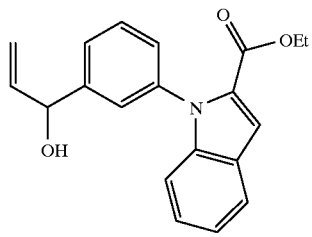

167

To a stirred solution 1.2 g (3.7 mmole) of 167 and 0.5 ml (4.8 mmole) of 2,6-lutidine in methylene chloride at 0° C. was added 1.2 ml (4.4 mmole) of triisopropylsilyltrifluoromethane sulfonate dropwise. The mixture was stirred for twenty minutes at 0° C. The reaction was diluted with methylene chloride and washed two times with aqueous potassium bisulfate, two times with water, once with brine and dried over magnesium sulfate. The solvent was evaporated under reduced pressure to give 1.7 g of 168.

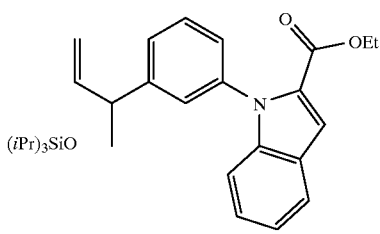

168

To a stirred mixture of 170 mg (4.5 mmole) of lithium aluminum hydride in THF (5 ml) at 0° C. was added 1.7 g (3.6 mmole) of 168 in THF (3 ml). The mixture was stirred for fifteen minutes and was slowly quenched with aqueous sodium sulfate, then warmed to room temperature and treated with excess of sodium sulfate powder. The mixture was stirred for fifteen minutes and filtered. The solvent was evaporated under reduced pressure and the residue was purified by chromatography on silica gel using 95:5 hexane/ethyl acetate to give 0.86 g of 169.

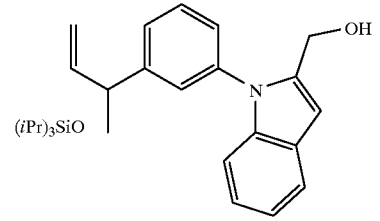

169

To a stirred mixture of 62 mg (2.6 mmole) of sodium hydride in THF (6 ml) at 0° C. was added 0.86 g (2.0 mmole) of 169. The mixture stirred for twenty minutes and then treated with 0.4 ml (5.0 mmole) of iodoethane, allowed to warm to room temperature and stir overnight. The reaction was recooled to 0° C. and slowly quenched with water. Partitioned with water and ethyl acetate. The organic phase was washed two times with water, once with brine, and dried over magnesium sulfate. The solvent was evaporated under reduced pressure to give 0.92 g of 170.

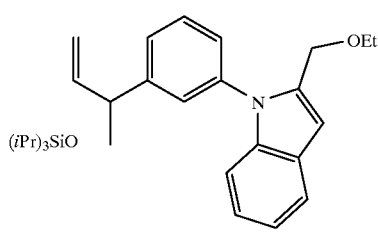

170

To a stirred solution of 0.92 g (2.0 mmole) of 170 in THF (5 ml) at 0° C. was added 2.4 mL (2.4 mmole) of 1M tetrabutylammonium fluoride in THF. The reaction was allowed to warm to room temperature and stir for two hours. Partitioned with ethyl acetate and dilute hydrochloric acid. The organic phase was then washed two times with dilute hydrochloric acid, once with brine, and dried over magnesium sulfate. The residue was purified by chromatography on silica gel using 3:1 hexane:diethyl ether as eluent to give 470 mg of 171.

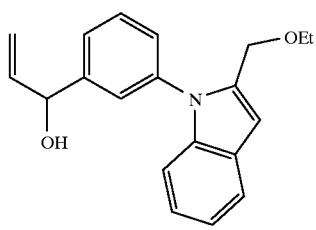

171

To a stirred mixture of 450 mg (1.5 mmole) of 171, 1.3 g of 4 Å powdered sieves, and 0.25 mL (2.9 mmole) of morpholine in methylene chloride (15 mL) was added 1.3 g (15 mmole) of manganese(IV)oxide. The mixture was allowed to stir for two hours at room temperature. The reaction was filtered through celite and evaporated under reduced pressure to give 448 mg of 172.

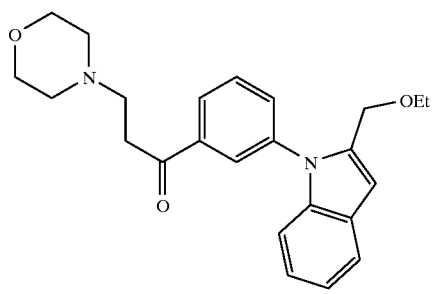

172

To a stirred mixture of 43 mg (1.14 mmole) of lithium aluminum hydride in THF (4 ml) at −78° C. was added 448 mg (1.14 mmole) of 172 dissolved in THF (4 ml). The mixture was allowed to stir for two hours and was slowly quenched with aqueous sodium sulfate, then warmed to room temperature and and treated with excess of sodium sulfate powder. The mixture was stirred for fifteen minutes and filtered. The solvent was evaporated under reduced pressure to give 450 mg of 173.

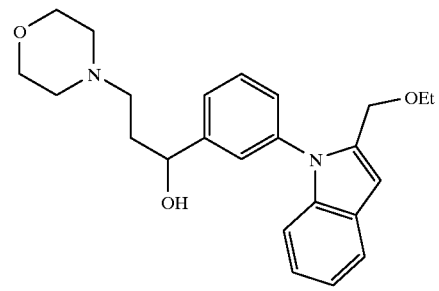

173

To a stirred solution of 450 mg (1.15 mmole) of 173, 565 mg (3.40 mmole) of (+)-(s)-α-methoxyphenylacetic acid, and catalytic 4-dimethylaminopyridine in methylene chloride (7 ml) was added 650 mg (3.4 mmole) of 1-(3-dimethylaminopropyl)-3-ethylcarbodiimide hydrochloride. The reaction was allowed to stir at room temperature overnight, diluted with methylene chloride and washed two times with aqueous sodium bicarbonate, two times with water, once with brine, and dried over sodium sulfate. The solvent was evaporated under reduced pressure and the residue was purified by chromatography on silica gel using diethyl ether as eluent to give 260 mg of the desired higher Rf diastereomer, 174.

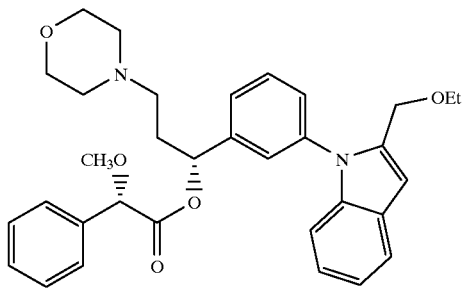

174

To a stirred mixture of 18 mg (0.48 mmole) of lithium aluminum hydride in diethyl ether (1 ml) at −78° C. was added 174 dissolved in diethyl ether (1 ml). The mixture was allowed to stir for two minutes and was quenched with aqueous sodium sulfate, then warmed to room temperature and treated with excess of sodium sulfate powder. The mixture was stirred for fifteen minutes and filtered. The solvent was evaporated under reduced pressure and the residue was purified by chromatography on silica gel using 3:97 ethyl alcohol/ethyl acetate as eluent to give 154 mg of 175.

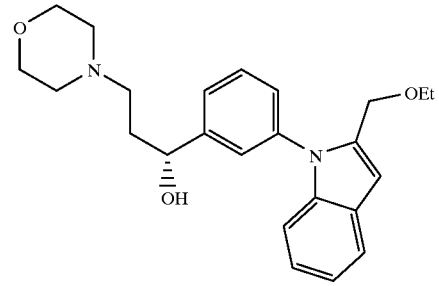

175

To a stirred solution of 250 mg (1.02 mmole) of 147 in methylene chloride at 0° C. was added 3.08 ml (3.08 mmole) of 1M tert-butylmagnesium chloride in THF. The reaction was allowed to stir at 0° C. for fifteen minutes and quenched with aqueous ammonium chloride. The aqueous phase was extracted three times with methylene chloride. The organic layers were combined and washed once with brine, dried over magnesium sulfate, and the solvent was evaporated under reduced pressure. The residue was purified by chromatography on silica using 9:1 hexane/ethyl acetate as eluent to give 102 mg of 176.

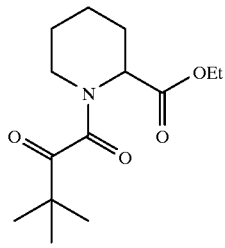

176

To a stirred solution of 102 mg (0.38 mmole) of 176 in THF (1 mL) at 0° C. was added 0.76 ml (0.76 mmole) of 1N lithium hydroxide. The reaction was allowed to warm to room temperature and stir for four hours, then acidified with 10% aqueous potassium bisulfate, and extracted three times with methylene chloride. The organic layers were combined and washed once with brine, dried over magnesium sulfate, and the solvent was evaporated under reduced pressure to give 85 mg of 177.

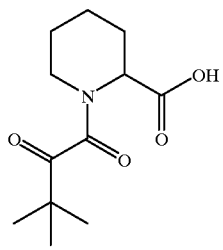

177

To a stirred solution of 20 mg (0.051 mmole) of 175, 18 mg (0.076 mmole) of 177, 18 mg (0.086 mmole) of dicyclohexyl carbodiimide, and catalytic camphorsulfonic acid in methylene chloride (1 ml) at room temperature was added catalytic N,N-dimethylaminopyridine. The reaction was allowed to stir overnight. The solvent was evaporated under reduced pressure and purified by chromatography on silica using 3:2 ethyl acetate/hexane to give 23 mg of 82. TLC Rf: 0.12 (3:2 ethyl acetate/hexane), $^1$HNMR (500 MHz, CDCl$_3$): δ 1.14 (s,3H), 1.23 (s, 9H), 1.25–1.38 (m, 1H) 1.40–1.56 (m, 1H), 1.57–1.80 (m, 3H), 2.0 (m, 1H), 2.20 (m,1H), 2.30–2.47 (m, 6H), 3.17 (m, 1H), 3.29 (m, 2H), 3.44 (q, 2H), 3.69 (m, 4H), 4.45 (m, 2H), 5.29 (m, 1H), 5.97 (t, 1H), 6.67 (s, 1H), 7.15 (m, 3H), 7.44 (m, 3H), 7.52 (d, 1H), 7.64 (d, 1H).

EXAMPLE 5

Preparation of Compound 94

To a solution of 16 g (157 mmole) of 2,3-

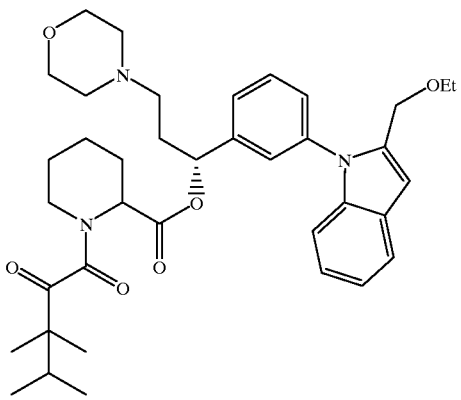

94 dimethyl-2-butanol and 20.4 g (235 mmole) of lithium bromide at 0° C. was added 36.4 ml (314 mmole) 48% aqueous hydrobromic acid dropwise. The reaction was allowed to stir for two hours and then warmed to room temperature. The organic phase was washed three times with ethylene glycol dried over sodium sulfate to give 20 g of 176.

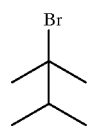

176

To a solution of 5 g (30.0 mmole) of 176 in THF (5 ml) was added 810 mg (33.3 mmole) of magnesium turnings. After initial exotherm, the reaction was heated to reflux for one hour. The solution was cooled to room temperature and added to 900 mg (3.7 mmole) of 147 in methylene chloride (5 ml) and allowed to stir overnight. The reaction was cooled to 0° C. and acidified with 0.5N aqueous hydrochloric acid, washed organic phase two times with water, once with aqueous sodium bicarbonate, two times with water, once with brine, and dried over sodium sulfate. The solvent was evaporated under reduced pressure and the residue was purified by chromatography on silica using 9:1 hexane/ethyl acetate to give 121 mg of 177.

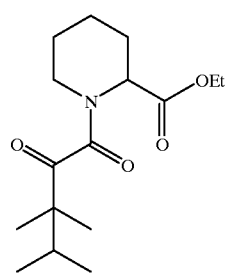

177

To a solution of 121 mg (0.41 mmole) of 177 in THF (1 ml) at 0° C. was added 1.0 ml (1.04 mmole) of 1N aqueous lithium hydroxide dropwise. The reaction was allowed to warm to room temperature, stirred overnight, recooled to 0° C., acidified with 1.1 ml 1N hydrochloric acid, and extracted three times with benzene. The organic phase was cooled to 0° C., subjected to a stream of nitrogen for 0.5 hours and then dried over sodium sulfate. The solvent was evaporated under reduced pressure to give 95 mg or 178.

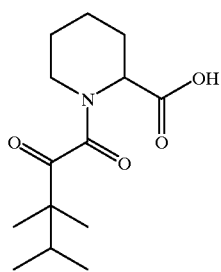

178

To a stirred solution of 13 mg (0.033 mmole) of 175, 14 mg (0.052 mmole) of 178, 12 mg (0.056 mmole) of dicyclohexyl carbodiimide, and catalytic camphorsulfonic acid in methylene chloride (1 ml) at room temperature was added catalytic N,N-dimethylaminopyridine. The reaction was allowed to stir overnight. The solvent was evaporated under reduced pressure and the product purified by chromatography on silica gel using 99:1 methylene chloride/ethyl alcohol to give 10 mg of 94. TLC Rf: 0.41 (95:5 diethyl ether/ethyl alcohol), $^1$HNMR (500 MHz, CDCl$_3$): δ 0.87 (d,6H), 1.13 (s, 6H), 1.28 (s, 3H), 1.29–1.82 (m, 6H), 2.02 (m, 1H), 2.15–2.30 (m, 2H), 2.32–2.48 (m, 6H), 3.14 (m, 1H), 3.38 (m, 1H), 3.44 (q, 2H), 3.71 (m, 4H), 4.45 (s, 2H), 5.3 (d, 1H), 5.97 (t, 1H), 6.68 (s, 1H), 7.13 (m, 3H), 7.45 (m, 3H), 7.54 (d, 1H), 7.65 (d, 1H).

EXAMPLE 6

Preparation of Compound 27

To a solution of 31.05 g (225 mmol) of 1,3-1-benzenedemethanol (Aldrich Chemical Co.) in 500 mL of dry THF was added 7.76 g (232 mmol) of 80% sodium hydride. To this suspension was added 34.97 (232 mmol) of tert-butyldimethylsilyl chloride and the resulting mixture was allowed to stir overnight at room temperature. The reaction mixture was then quenched with water, extracted into ethyl acetate, dried over MgSO$_4$ and concentrated. Flash chromatography (elution with 5:1 hexane/ethyl acetate) gave 33.3 g of the alcohol (179) (59%).

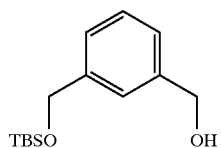

179

To a solution of 33.2 g (131.5 mmol) of the alcohol (179) in 100 mL of CH$_2$Cl$_2$ at 0° C. was added 350 mg (2.2 mmol) of TEMPO, 295 mL (197 mmol) of 0.67 M sodium hypochlorite containing 7.5 g of sodium bicarbonate and 1.34 g (13.1 mmol) of sodium bromide. The resulting mixture was allowed to stir at 0° C. for 0.5 h and then extracted into ethyl acetate. The organic phase was washed sequentially with aqueous solutions of potassium iodide and sodium thiosulfate and then dried over MgSO$_4$ and concentrated. Flash chromatography (elution with 20% ethyl acetate in hexane) gave 31.4 g (95%) of the aldehyde 180.

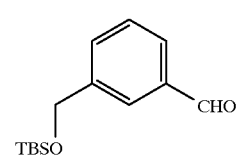

180

To a solution of 8.1 g (51.1 mmol) of 3-bromopyridine in 100 mL of dry ether at –78° C. was added 31 mL of a 1.6 M hexane solution of n-BuLi (31 ml) and the resulting mixture was allowed to stir at –78° C. for 20 min. To this solution was added a solution of 12.8 g (51.1 mmol) of aldehyde 180 in 190 mL of dry ether and this solution was then allowed to stir at –78° C. for 1 h. The reaction mixture was poured into saturated aqueous NH$_4$Cl, the layers were separated and the aqueous layer was extracted with ether. The organic layers were combined, dried over Na$_2$SO$_4$, filtered and concentrated under reduced pressure. The obtained residue was chromatographed on silica gel with hexane/ethyl acetate (5:3) to give 12 g (71%) of alcohol 181 as a colorless oil. NMR (500 MHZ, CDCl3) 0.06 (6H,s) 0.91(9H,s) 4.71 (2H,s) 5.83 (1H,s) 7.68 (6H,m) 8.40 (1H,m) 8.52 (1H,d,J=2.3 Hz).

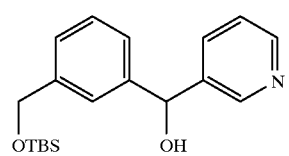

181

A mixture of 12 g (36.4 mmol) of alcohol 181, 21 g (241.5 mmol) of MnO$_2$ and 6.8 g of 4 Å molecular sieves in 90 mL of CH$_2$Cl$_2$ was allowed to stir overnight at room temperature. The reaction mixture was filtered through celite and concentrated under reduced pressure to give 10.8 g (90%) of ketone 182 as a colorless oil. NMR (500 MHz,CDCl3) 0.06 (6H, s) 0.89 (9H,s) 4.76 (2H,s) 7.3–7.7 (6H,m) 8.77 (1H,d, J=1.7 Hz) 8.95 (1H,d,J=1.7 Hz).

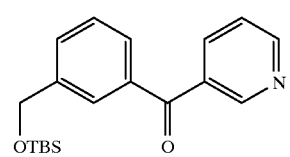

182

To a suspension of 8.1 g (20.28 mmol) of n-butyltriphenylphosphonium bromide in 120 mL of dry THF was added 11.5 mL of a 1.6 M hexane solution of n-BuLi at 0° C. and the resulting red solution was stirred at 0° C. for 30 min. To this solution was added 4.0 g (12.21 mmol) of ketone 182 in 10 mL of dry THF at 0° C. and this mixture was warmed to room temperature over a period of an hour. Flash chromatography (elution with 3:1 hexane-:ethyl acetate) gave a mixture of the E-olefin 183 and the corresponding Z-olefin isomer. This mixture was further chromatographed on silica gel with hexane/ethyl acetate (4:1) to give pure olefin 183 (970 mg,19%) as a colorless oil. NMR (500 MHZ, CDCl3) 0.08 (6H,s) 0.91 (12H,m) 1.4–1.6

(2H,m) 2.1–2.2 (2H,m) 4.75 (2H,s) 6.11 (1H,t,J=7.4 Hz) 7.0–7.5 (6H,m) 8.44 (1H,d,J=4.5 Hz) 8.54 (1H,d,J=1.1 Hz).

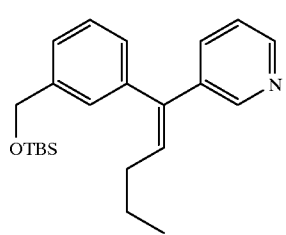

183

A mixture of 960 mg (2.61 mmol) of olefin (183) and 13 mL of a 1 M solution of tetrabutylamonium fluoride in THF stirred for 30 min at room temperature. This mixture was then poured into water and extracted with ethyl acetate. The organic layer was dried over Na$_2$SO$_4$, filtered and concentrated under reduced pressure. The residue was chromatographed on silica gel with hexane/ethyl acetate (5:1) to give alcohol 184 (700 mg,87%) as a colorless oil. NMR (500 MHz,CDCl3) 0.88 (3H,m) 1.37 (2H,m) 2.025 (2H,m) 4.69 (2H s) 6.12 (1H,t,J=7.4 Hz) 7.0–7.5 (6H,m) 8.33 (1H, m) 8.46 (1H,d,J=2.2 Hz).

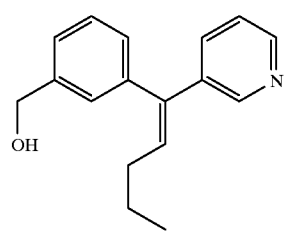

184

A mixture of 579 mg (2.24 mmol) of alcohol 184, 1.2 g (13.8 mmol) of MnO$_2$ and 1.0 g of 4 Å molecular sieves in 10 mL of CH$_2$Cl$_2$ was stirred overnight at room temperature. This mixture was then filtered and the filtrate was concentrated under reduced pressure to give aldehyde (185) (560 mg,99%) as a colorless oil. NMR (500 MHZ, CDCl3) 0.91 (3H,m) 1.50 (2H,m) 2.09 (2H,m) 6.22 (1H,t,J=7.4 Hz) 7.1–7.9 (6H,m) 8.4–8.6 (2H,m) 10.03 (1H,s).

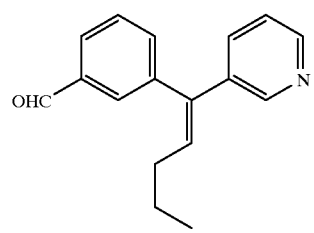

185

To a solution of 560 mg (2.23 mmol) of aldehyde 185 in 10 mL of dry THF at −10° C. was added 4.5 mL of a 1 M THF solution of vinyl magnesium bromide dropwise and the resulting mixture was stirred at −10° C. for 30 min. The mixture was then poured into saturated aqueous NH$_4$Cl and extracted with CHCl$_3$. The organic layer was dried over Na$_2$SO$_4$, filtered and concentrated under reduced pressure. The residue was chromatographed on silica gel with hexane/ethyl acetate (1:1) to give allyl alcohol 186 (310 mg,50%) as a colorless oil. NMR (500 MHZ, CDCl3) 0.89 (3H,t,J=7.3 Hz) 1.46 (2H,m) 2.10 (2H,m) 5.1–5.3 (3H,m) 5.9–6.2 (2H, m) 7.0–7.2 (3H,m) 7.3–7.5 (3H,m) 8.33 (1H,m) 8.44 (1H, d,J=2.4 Hz)

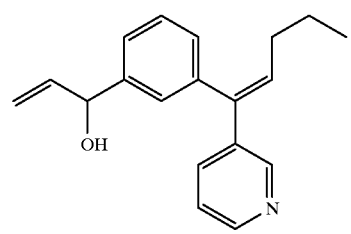

186

A mixture of 310 mg (1.12 mmol) of allyl alcohol 186, 488 mg (5.61 mmol) of MnO2 and 500 mg of 4 Å molecular sieves was stirred overnight at room temperature. The reaction mixture was then filtered and the filtrate was concentrated under reduced pressure to give enone 187 (244 mg,79%) as a colorless oil. NMR (500 MHZ, CDCl3) 0.92 (3H,t,J=7.3 Hz), 1.50 (2H,m) 2.11 (2H, m) 5.93 (1H, m) 6.22 (1H,t,J=7.4 Hz) 6.44 (1H, m) 7.1–7.3 (2H,m) 7.3–7.6 (3H, m) 7.76 (1H,s) 7.92 (1H, m) 8.4–8.6 (2H,m).

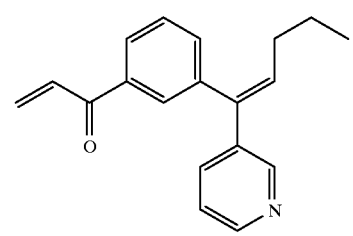

187

A mixture of 244 mg (0.88 mmol) enone 187, 153 mg (1.75 mmol) of morpholine (153 mg) and 1.83 mL (13.13 mmol) of triethylamine in 5.0 mL of CH$_3$CN was stirred for 30 min at room temperature and the mixture was then concentrated under reduced pressure. The residue was chromatographed on silica gel with CHCl$_3$/MeOH (100:3) to give ketone (188) (240 mg,75%) as a colorless oil. NMR (500 MHz, CDCl3) 0.91 (3H,t,J=7.3 Hz) 1.4–1.6 (2H,m) 2.0–2.2 (2H,m) 2.44 (4H,m) 2.82 (2H,t,J=6.8 Hz) 3.17 (2H,t,J=6.8 Hz) 3.70 (4H,m) 6.19 (1H,t,J=7.3 Hz) 7.1–7.6 (4H,m) 7.76 (1H,m) 7.91 (1H,m) 8.49 (2H,m).

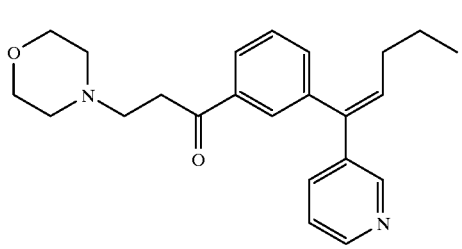

188

To a solution of 240 mg (0.67 mmol) of ketone (188) in 5.0 mL of MeOH at 0° C. was added 25 mg (0.67 mmol) of NaBH$_4$ and the resulting mixture was stirred at 0° C. for 30 min. The reaction mixture was then poured into saturated aqueous NH$_4$Cl and extracted with CHCl$_3$. The organic layer was dried over Na$_2$SO$_4$, filtered and conccectrated under reduced pressure. The residue was chromatographed on silica gel with CHCl$_3$/MeOH (100:3) to give alcohol (189) (208 mg,85%) as a colorless oil. NMR (500 MHZ, CDCl3) 0.94 (3H,t,J=7.3 Hz) 1.4–1.6 (2H,m) 1.8–2.0 (2H, m) 2.0–2.2 (2H,m) 2.4–2.7 (6H,m) 3.71 (4H,m) 4.93 (1H,m) 6.11 (1H,t,J=7.3 Hz) 7.0–7.2 (2H,m) 7.3–7.5 (4H,m) 8.41 (1H,m) 8.50 (1H,d,J=1.5 Hz).

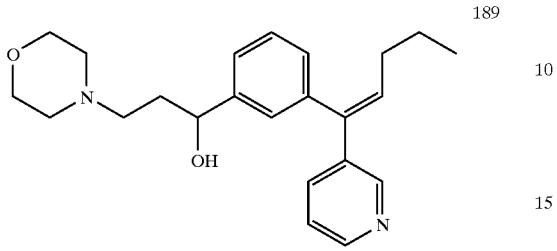

189

To a solution of 141 mg (0.61 m-mol) of Boc-L-pipecolic acid in 2.0 mL of CH₂Cl₂ and 2.0 mL of DMF was added 205 mg (0.56 mmol) of alcohol (189), 119 mg (0.62 mmol) of EDC and a catalytic amount of DMAP. The mixture was stirred overnight at room temperature and was then poured into water. The layers were separated and the organic layer was dried over Na₂SO₄, filtered and concentrated under reduced pressure. The residue was chromatographed on silica gel with CHCl₃/MeOH (100:1) to give ester (190) (207 mg,64%) as a colorless oil. NMR (500 MHZ, CDCl3) 0.91 (3H,t,J=7.3 Hz) 1.2–1.8 (15H,m) 1.8–2.0 (1H,m) 2.0–2.3 (4H,m) 2.3–2.5 (6H,m) 2.7–2.9 (2H,m) 3.67 (4H,m) 3.7–4.1 (1H,m) 4.7–4.9 (1H,m) 5.90 (1H,m) 6.14 (1H,t,J= 7.3 Hz) 7.1–7.2 (3H,m) 7.3–7.5 (3H,m) 8.4–8.5 (2H,m).

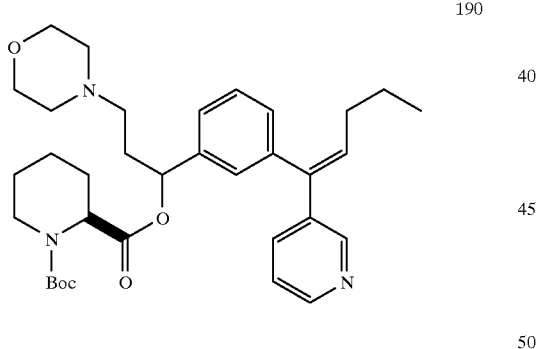

190

To a solution of 207 mg (0.36 mmol) of ester (190) in 1.5 mL of CH₂Cl₂ at room temperature was added 3.2 mL of trifluoroacetic acid and the mixture was stirred for 1 h at room temperature. The reaction mixture was then neutralized by the dropwise addition of saturated aqueous K₂CO₃. The layers were separated and the organic layer was dried over Na₂SO₄, filtered and concentrated to give amine (191) (155 mg,89%) as a pale brown oil. NMR (500 MHZ, CDCl3) 0.95 (3H,t,J=7.3 Hz) 1.3–1.7 (6H,m) 1.7–2.1 (2H, m) 2.1–2.3 (3H,m) 2.3–2.5 (8H,m) 2.5–2.7 (1H,m) 3.0–3.1 (1H,m) 3.3–3.5 (1H,m) 3.67 (4H,m) 5.89 (1H,m) 6.13 (1H,t,J=7.3 Hz) 7.0–7.2 (3H,m) 7.3–7.5 (3H,m) 8.44 (2H, m).

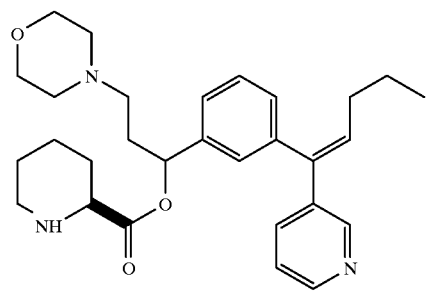

191

To a solution of 155 mg (0.32 mmol) of amine (191) in 2.8 mL of CH₂Cl₂ at room temperature was added 80 mg (0.33 mmol) of 3,4,5-trimethoxybenzoylformic acid and 92 mg (0.48 mmol) of EDC. After stirring overnight at room temperature, the reaction mixture was partitioned with water and the organic was dried over Na₂SO₄, filtered and concentrated The residue was chromatographed on silica gel with CHCl₃/MeOH (100:5) to give the diastereomeric amides (27) (166 mg, 74%) as a mixture of rotamers. NMR (500 MHZ, CDCl3) 1.8–2.0 (3H,m) 1.4–1.6 (6H,m) 1.6–1.9 (2H,m) 2.0–2.2 (3H,m) 2.2–2.5 (7H,m) 3.0–3.3 (1H,m) 3.3–3.5 (1H,m) 3.68 (4H,m) 3.8–4.0 (9H,m) 5.38 (1H,d,J= 3.8 Hz) 5.90 (1H,m) 6.14 (1H,m) 7.1–7.3 (3H,m) 7.3–7.5H, m) 8.42 (2H,m). The two diastereomeric mixture was further separated by HPLC (ODS coloum with 73:27 MeOH— H2O) to give 38 mg and 21 mg of each isomer.

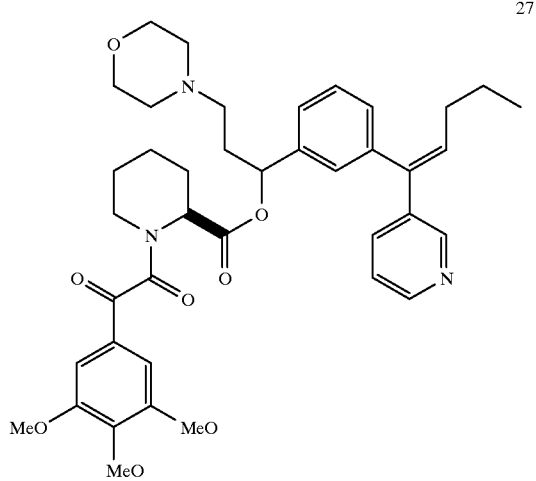

27

EXAMPLE 7

MDR Sensitization Assays

To assay the ability of the compounds according to this invention to increase the antiproliferative activity of a drug, cell lines which are known to be resistant to a particular drug may be used. These cell lines include, but are not limited to, the L1210, P388D, CHO and MCF7 cell lines. Alternatively, resistant cell lines may be developed. The cell line is exposed to the drug to which it is resistant, or to the test compound; cell viability is then measured and compared to the viability of cells which are exposed to the drug in the presence of the test compound.

To carry out assays using L1210 mouse leukemia cells transformed with the pHaMDR1/A retrovirus carrying a MDR1 cDNA, we follow the procedure described by Pastan et al., *Proc. Natl. Acad. Sci.*, Vol. 85, 448614 4490 (1988). The resistant line, labelled L1210VMDRC.06, is obtained from Dr. M. M. Gottesman of the National Cancer Institute. Drug-resistant transfectants are selected by culturing cells in 0.06 mg/ml colchicine.

Multi-drug resistance assays are conducted by plating cells ($2 \times 10^3$, $1 \times 10^4$, or $5 \times 10^4$ cells/well) in 96 well microtiter plates and exposing them to a concentration range of doxorubicin (50 nM–10 µM) in the presence or absence of multi-drug resistance modifier compounds ("MDR inhibitors") of this invention (1, 2.5 or 10 µM) as described in Ford et al., *Cancer Res.*, Vol. 50, 1748–1756. (1990). After culture for 3 days, the viability of cells is quantitated using MTT (Mossman) or XTT dyes to assess mitochondrial function. Also see, Mossman T., *J. Immunol. Methods*, Vol. 65, 55–63 (1983).

Proton nuclear magnetic resonance ($^1$H NMR) spectra are recorded at 500 MHz on a Bruker AMX 500. Chemical shifts are reported in parts per million (δ) relative to Me$_4$Si (δ0.0). Analytical high performance liquid chromatography is performed on either a Waters 600E or a Hewlett Packard 1050 liquid chromatograph.

Results are determined by comparison of the IC$_{50}$ for doxorubicin alone to the IC$_{50}$ for doxorubicin+MDR inhibitor. An MDR ratio is calculated (IC$_{50}$ Dox/ IC$_{50}$ Dox+ Inhibitor) and the integer value used for comparison of compound potencies.

Compounds according to this invention were tested for intrinsic antiproliferative or cytotoxic activity. The results are summarized in Table 2 below.

TABLE 2

| Compound # | Date | IC50 DXR Alone (nM) | IC50 (DXR + 2.5 µM VA) (nM) | MDR Ratio |
|---|---|---|---|---|
| 22 | 5/12/95 | 700 | 550 | 1.3 |
| 22 | 4/21/95 | 2100 | 170 | 12.4 |
| 24 | 5/12/95 | 700 | <50 | >14.0 |
| 26 | 5/12/95 | 700 | 80 | 8.8 |
| 27 | 5/12/95 | 700 | 55 | 12.7 |
| 28 | 5/12/95 | 700 | 70 | 10.0 |
| 30 | 5/12/95 | 700 | 50 | 14.0 |
| 32 | 5/12/95 | 700 | 60 | 11.7 |
| 40 | 5/12/95 | 700 | 280 | 2.5 |
| 43 | 5/12/95 | 700 | 50 | 14.0 |
| 52 | 5/12/95 | 700 | 170 | 4.1 |
| 52 | 4/21/95 | 2100 | 360 | 5.8 |
| 59 | 5/12/95 | 700 | 65 | 10.8 |
| 61 | 5/12/95 | 700 | 280 | 2.5 |
| 71 | nd | | | |
| 76 | 5/12/95 | 700 | 110 | 6.4 |
| 79 | 5/12/95 | 700 | 90 | 7.8 |
| 89 | 5/12/95 | 700 | 140 | 5.0 |
| 90 | 5/12/95 | 700 | 95 | 7.4 |
| 91 | 5/12/95 | 700 | 260 | 2.7 |
| 100 | 5/12/95 | 700 | <50 | <14.0 |
| 101 | nd | | | |
| 105 | 5/12/95 | 700 | 130 | 5.4 |
| 107 | 5/12/95 | 700 | 80 | 8.8 |
| 110 | nd | | | |
| 111 | 5/12/95 | 700 | 75 | 9.3 |
| 112 | 5/12/95 | 700 | 65 | 10.8 |
| 113 | 5/12/95 | 700 | 100 | 7.0 |
| 119 | 5/12/95 | 700 | 700 | 1.0 |
| 123 | 4/21/95 | 2100 | 170 | 12.4 |

EXAMPLE 8

Inhibition of MRP-Mediated MDR

In order to demonstrate that the compounds of this invention are effective in reversing MPR-mediated MDR, in addition to P-glycoprotein-mediated MDR, we assay inhibition in a non-P-glycoprotein expressing cell line.

We plate HL60/ADR cells in 96 well microtiter plates ($4 \times 10^4$ cells/well) The cells are then exposed to various concentrations of doxorubicin (50 nM to 10 µM) in the presence or absence of various compounds of this invention at various concentrations (0.5–10 µM). After culturing the cells for 3 days, their viability is quantitated using the XTT dye method to assess mitochondrial function. Results are expressed as a ratio of the IC$_{50}$ for doxorubicin alone to the IC$_{50}$ for doxorubicin plus MDR inhibitor. IC$_{50}$ values are expressed in nM. The results indicate that MRP-mediated MDR is inhibited by compounds of this invention.

EXAMPLE 9

FKBP12 Binding Assay

The inhibition of FKBP rotomase activity by the preferred FKBP12 binding compounds present in the compositions of this invention was assayed. In this assay various quantities of FKBP12 binding compound (0nM–10 µM) were added to cis-N-succinyl-Ala-Ala-Pro-Phe-p-nitroanilide in the presence of FKBP12 and chymotrypsin. FKBP12 converts the cis form of the substrate to the trans form. This allows chymotrypsin to cleave p-nitroanilide from the substrate. Release of p-nitroanilide was measured spectrophotometrically. This assay allowed me to measure the change in the first order rate constant of the rotomase activity as a function of FKBP12 binding compound concentration and yielded an estimate of apparent K$_i$. The most preferred FKBP12 binding compounds utilized in this compositions and methods of this invention and their calculated K$_i$ are tabulated below.

| Cmpd # | K$_i$ (nM) | Cmpd # | K$_i$ (nM) | Cmpd # | K$_i$ (nM) | Cmpd # | K$_i$ (nM) |
|---|---|---|---|---|---|---|---|
| 3 | 300 | 36 | >30 | 69 | 745 | 102 | 700 |
| 4 | >5000 | 37 | <1 | 70 | 45 | 103 | 21 |
| 5 | 4000 | 38 | 70 | 71 | 364 | 104 | 870 |
| 6 | 24 | 39 | 45 | 72 | 225 | 105 | 94 |
| 7 | >10000 | 40 | 500 | 73 | 718 | 106 | 2100 |
| 8 | 1000 | 41 | 67 | 74 | 500 | 107 | 7600 |
| 9 | 7 | 42 | 2100 | 75 | 188 | 108 | 5100 |
| 10 | 16 | 43 | 180 | 76 | 400 | 109 | >10000 |
| 11 | 7 | 44 | 53 | 77 | 2100 | 110 | >30000 |
| 12 | 30 | 45 | 230 | 78 | 77 | 111 | 800 |
| 13 | 5 | 46 | 100 | 79 | 12 | 112 | 930 |
| 14 | 12 | 47 | 84 | 80 | 230 | 113 | 61 |
| 15 | 1 | 48 | 120 | 81 | 189 | 114 | 172 |
| 16 | 3300 | 49 | >10000 | 82 | 38 | 115 | 44 |
| 17 | 0.6 | 50 | >10000 | 83 | 315 | 116 | 130 |
| 18 | 0.4 | 51 | >10000 | 84 | 2000 | 117 | 150 |
| 19 | 27 | 52 | 200 | 85 | 1.0 | 118 | 70 |
| 20 | 5.8 | 53 | 70 | 86 | 14 | 119 | >5000 |
| 21 | 90 | 54 | >50000 | 87 | 2.3 | 120 | 80 |
| 22 | 31 | 55 | >10000 | 88 | 64 | 121 | 85 |
| 23 | 2500 | 56 | >5000 | 89 | 263 | 122 | 32 |
| 24 | 0.5 | 57 | 930 | 90 | 9 | 123 | 2800 |
| 25 | 30 | 58 | >9000 | 91 | 8 | 124 | 1000 |
| 26 | 2.4 | 59 | 71 | 92 | 32 | 125 | 1100 |
| 27 | 260 | 60 | 57 | 93 | 44 | 126 | 3000 |
| 28 | 20 | 61 | >10000 | 94 | 16 | 127 | 19 |
| 29 | 1 | 62 | 100 | 95 | 14 | 128 | 41 |
| 30 | 27 | 63 | >5000 | 96 | 28 | 129 | 1200 |
| 31 | 130 | 64 | 340 | 97 | 930 | 130 | 490 |
| 32 | 9.8 | 65 | 490 | 98 | 62 | 131 | 90 |
| 33 | 12 | 66 | 55 | 99 | ND | 132 | >10000 |
| 34 | 6 | 67 | 270 | 100 | 380 | 133 | 315 |
| 35 | 380 | 68 | >5000 | 101 | 500 | | |

EXAMPLE 10

Assay of Neurite Outgrowth in PC12 Cultures

The ability of the compounds of this invention to bind to FKBP-12 and inhibit its rotomase activity suggested that these compounds could also stimulate nerve growth.

In order to directly determine the neurotrophic activity of the compounds utilized in this invention, the assay described by W. E. Lyons et al., *Proc. Natl. Acad. Sci. USA*, 91, pp. 3191–95 (1994) is carried out.

PC12 rat pheochromocytoma cells are maintained at 37° C. and 5% $CO_2$ in Dulbecco's modified Eagle's medium (DMEM) supplemented with 10% heat-inactivated horse serum (HS) and 5% heat-inactivated fetal bovine serum (FBS). The cells are then plated at $10^5$ per 35mm culture well coated with 5 µg/cm² rat tail collagen and allowed to attach. The medium is then replaced with DMEM+2% HS and 1% FBS, NGF (1–100 ng/ml) and varying concentrations of an FKBP12 binding compound (0.1 nM–10 µM). Control cultures are administered NGF without FKBP12 binding compound.

The compounds of this invention are able to increase neurite outgrowth in these cells over and above the outgrowth caused by NGF alone.

EXAMPLE 11

Assay of Neurite Outgrowth in Dorsal Root Ganglion Culture

Another way to directly determine the neurotrophic activity of the FKB12 binding compounds utilized in this invention is the dorsal root ganglion culture assay also described by W. E. Lyons et al., *Proc. Natl. Acad. Sci. USA*, 91, pp. 3191–95 (1994).

In this assay, dorsal root ganglia are dissected from 16 day rat embryos and cultured in collagen-coated 35 mm dishes with N2 medium at 37° C. in a 15% $CO_2$ environment. Sensory ganglia are then treated with various concentrations of NGF (0–100 ng/ml) and an FKB12 binding compound (0.1 nM–10 µM). Ganglia are observed every two days under a phase contrast microscope and axon lengths are measured. Control cultures either lack FKBP12 binding compound or lack FKBP12 binding compound and NGF.

The FKBP12 binding compounds utilized in this invention cause an increase in neurite outgrowth over control cultures which lack such compounds in both the presence and absence of NGF.

While we have hereinbefore presented a number of embodiments of this invention, it is apparent that our basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:

1. A compound of formula (I):

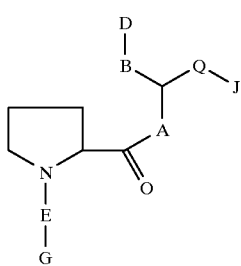

wherein:

A is $CH_2$, O, NH or N—[(C1–C4)-alkyl];

B is (C1–C6)-straight or branched alkyl, or (C2–C6)-straight or branched alkenyl or alkynyl, wherein one of the carbon atoms of B is optionally replaced by O, S, SO, $SO_2$, NH or N—[(C1–C4)-alkyl];

D is 1-[(C1–C4)-alkyl]-4-piperidinyl; N-morpholinyl, 1-piperazinyl; 1-[(C1–C4)-alkyl]-4-piperazinyl; a 5–7-membered cycloalkyl or cycloalkenyl ring optionally comprising substituents at the 3 and/or 4 position of said ring, wherein said substituents are selected from oxo, OH, (C1–C4)-alkyl, O—[(C1–C4)-alkyl], O—[(C2–C4)-alkenyl], $NH_2$, N,N di-[(C1–C4)-alkyl] amino or halogen; or a monocyclic or bicyclic aromatic ring structure consisting of 5 to 6 members in each ring and optionally comprising up to 4 heteroatoms independently selected from N, O or S;

E is $SO_2$ or —C(O)—C(O)—;

G is 1-[(C1–C4)-alkyl]-4-piperidinyl, 1-piperazinyl, 1-[(C1–C4)-alkyl]-4-piperazinyl, (C1–C7)-straight or branched alkyl, (C2–C7)-straight or branched alkenyl or alkynyl, (C5–C7)-cycloalkyl, or a monocyclic or bicyclic aromatic ring structure consisting of 5 to 6 members in each ring; wherein up to two carbon atoms in any G are optionally replaced independently by O, S, SO, $SO_2$ or N;

wherein G optionally comprises up to three substituents independently selected from halogen, hydroxyl, (C1–C6)-straight or branched alkyl, (C2–C6)-straight or branched alkenyl, O—[(C1–C5)-straight or branched alkyl], O—[(C2–C5)-straight or branched alkenyl], O-benzyl, amino, carboxyl, N—[(C1–C5)-straight or branched alkyl], N—[(C2–C5)-straight or branched alkenyl], trifluoromethyl or trifluoromethoxy; and wherein one carbon atom of any individual substituent is optionally replaced by O, N or S;

Q is a five membered aromatic ring containing 1 to 2 heteroatoms selected from N, O or S, or a six membered aromatic ring containing 0 to 2 heteroatoms selected from N, O or S;

J is a monocyclic or bicyclic aromatic ring structure attached to the 3 position of Q consisting of 5 to 6 members in each ring, optionally comprising up to four heteroatoms independently selected from O, S, or N; and wherein J optionally comprises up to 3 substituents independently selected from halo, OH, $CH_2OH$, $NO_2$, $SO_3H$, trifluoromethyl, trifluoromethoxy, O-phenyl, 1,2-methylenedioxy, $NR^1R^2$, amino, carboxyl, N—[(C1–C5)-straight or branched alkyl]-carboxamide, N—[(C2–C5)-straight or branched alkenyl]-carboxamide, N-morpholinocarboxamide, N-benzylcarboxamide, N-thiomorpholinocarboxamide, N-picolinoylcarboxamide, morpholinyl, piperidinyl, O—$R^3$, $CH_2$—$(CH_2)_q$—$R^3$, O—$(CH_2)_q$—$R^3$, $(CH_2)_q$—O—$R^3$, CH=CH—$R^3$, (C1–C6)-straight or branched alkyl, or (C2–C6)-straight or branched alkenyl, wherein in any substituent one carbon atom is optionally replaced by a heteroatom selected from the group consisting of O, S, SO, $SO_2$, NH or N—[(C1–C4)-alkyl];

wherein $R^1$ and $R^2$ are independently selected from the group consisting of hydrogen, (C1–C6)-straight or branched alkyl, (C2–C6)-straight or branched alkenyl or alkynyl and benzyl;

$R^3$ is selected from the group consisting of 4-methoxyphenyl, 2-pyridyl, 3-pyridyl, 4-pyridyl, pyrazyl, quinolyl, 3,5-dimethylisoxazoyl, 2-methylthiazoyl, thiazoyl, 2-thienyl, 3-thienyl and pyrimidyl; and q is 0–2;

provided that when E is —C(O)—C(O)—, J is not phenyl.

2. A compound of formula (II):

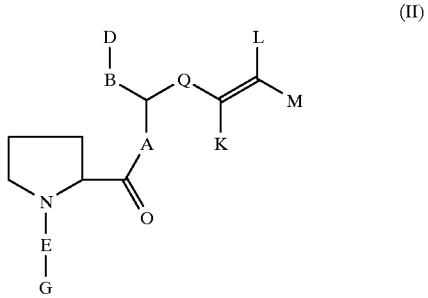

wherein:
- A, B, D, E, G and Q are as defined in claim 1;
- K is H, (C5–C7) cycloalkyl, (C5–C6) aromatic ring, 1-[(C1–C4)-alkyl]-4-piperidinyl, 1-piperazinyl, 1-[(C1–C4)-alkyl]-4-piperazinyl, (C1–C7)-straight or branched alkyl, (C2–C7)-straight or branched alkenyl or alkynyl, wherein up to two carbon atoms in K are optionally replaced independently by O, S, SO, $SO_2$, NH, NO or N—(C1–C4)-alkyl,
  wherein K optionally comprises up to 2 substituents independently selected from halo, amino, hydroxy, carboxy, methoxy or (C1–C3)alkyl; and
- L and M are independently selected from H, (C1–C7)-straight or branched alkyl, (C2–C7)-straight or branched alkenyl or alkynyl, wherein one carbon atom in L and M is optionally replaced by O, S, SO, $SO_2$, NH or N—(C1–C4)-alkyl,
  wherein L and M optionally comprise up to two substituents independently selected from halogen, hydroxy, amino, carboxy, or a 5 to 6 membered aromatic ring, said aromatic ring comprising up to two heteroatoms selected from N, O or S;
  provided that when E is —C(O)—C(O)—, K, L and M together with the carbon atoms to which they are bound do not form an unsubstituted (C2–C6) straight or branched alkenyl.

3. The compound according to claims 1 or 2, wherein no monocyclic or bicyclic ring in said compound comprises more than one heteroatom selected from O, S or N.

4. The compound according to claims 1 or 2, wherein:
A is oxygen; and
E is —C(O)—C(O)—.

5. A pharmaceutical composition comprising an amount of a compound according to claims 1 to 2 effective for the treatment or prevention of multi-drug resistance and a pharmaceutically acceptable carrier, adjuvant or vehicle.

6. The pharmaceutical composition according to claim 5, further comprising a chemotherapeutic agent.

7. The pharmaceutical composition according to claim 6, wherein said chemotherapeutic agent is selected from actinomycin D, doxorubicin, vincristine, vinblastine, etoposide, amsacrine, mitoxantrone, tenipaside, taxol or colchicine.

8. The pharmaceutical composition according to claim 5, further comprising a chemosensitizer.

9. The pharmaceutical composition according to claim 8, wherein said chemosensitizer is selected from cyclosporin A and its analogs, phenothiazines or thioxantheres.

10. A method for treating or preventing multi-drug resistance in a patient comprising the step of administering to said patient a pharmaceutical composition according to claim 6.

11. A pharmaceutically acceptable composition comprising:
  a) an amount of a compound according to claims 1 or 2 effective for stimulating neurite growth;
  b) a neurotrophic factor; and
  C) a pharmaceutically acceptable carrier, adjuvant or vehicle.

12. The composition according to claim 11, wherein said neurotrophic factor is selected from nerve growth factor (NGF), insulin growth factor (IGF) and active truncated derivatives thereof, acidic fibroblast growth factor (aFGF), basic fibroblast growth factor (bFGF), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3) and neurotrophin 4/5 (NT-4/5).

13. A method for stimulating neurite growth in nerve cells comprising the step of contacting said nerve cells with a composition according to claim 11.

14. The method according to claim 13, comprising the additional step of contacting said nerve cells with a neurotrophic factor.

15. The method according to claim 14, wherein said neurotrophic factor is selected from nerve growth factor (NGF), Insulin growth factor (IGF) and active truncated derivatives thereof, acidic fibroblast growth factor (aFGF), basic fibroblast growth factor (bFGF), platelet-derived growth factors (PDGF), brain-derived neurotrophic factor BDNF), ciliary neurotrophic factors (CNTF), glial cell line-derived neurotrophic factor (GDNF), neurotrophin-3 (NT-3) and neurotrophin 4/5 (NT-4/5).

16. The method according to claim 13, wherein said method is used to treat a patient who is suffering from or has suffered from Alzheimer's disease, Parkinson's disease, ALS, stroke and ischemia associated with stroke, neural paropathy, other neural degenerative diseases, motor neuron diseases, sciatic crush, spinal cord injuries or facial nerve crush.

* * * * *